(12) United States Patent
Bassett et al.

(10) Patent No.: US 11,667,669 B2
(45) Date of Patent: Jun. 6, 2023

(54) EPOXY-(METH)ACRYLATE MONOMERS AND POLYMERS AND METHODS OF MAKING AND USING THE SAME

(71) Applicants: ROWAN UNIVERSITY, Glassboro, NJ (US); THE UNITED STATES OF AMERICA AS REPRESENTED BY THE SECRETARY OF THE ARMY, Washington, DC (US)

(72) Inventors: Alexander W. Bassett, Mullica Hill, NJ (US); Joseph F. Stanzione, III, Wilmington, DE (US); John J. La Scala, Wilmington, DE (US)

(73) Assignees: Rowan University, Glassboro, NJ (US); The United States of America as represented by the Secretary of the Army, Washington, DC (US)

( * ) Notice: Subject to any disclaimer, the term of this patent is extended or adjusted under 35 U.S.C. 154(b) by 561 days.

(21) Appl. No.: 16/538,989

(22) Filed: Aug. 13, 2019

(65) Prior Publication Data
US 2020/0048301 A1 Feb. 13, 2020

Related U.S. Application Data

(60) Provisional application No. 62/718,007, filed on Aug. 13, 2018.

(51) Int. Cl.
| | | |
|---|---|---|
| *C07D 303/22* | (2006.01) | |
| *C07J 53/00* | (2006.01) | |
| *C08F 20/32* | (2006.01) | |
| *C07D 493/04* | (2006.01) | |

(52) U.S. Cl.
CPC .......... *C07J 53/002* (2013.01); *C07D 303/22* (2013.01); *C07D 493/04* (2013.01); *C08F 20/32* (2013.01)

(58) Field of Classification Search
None
See application file for complete search history.

(56) References Cited

FOREIGN PATENT DOCUMENTS

| KR | 20090088240 A | * | 2/2008 | ............... C08K 5/15 |
| WO | 2005108487 A1 | | 11/2005 | |

OTHER PUBLICATIONS

Baroncini, et al., "Recent advances in bio-based epoxy resins and bio-based epoxy curing agents", J Appl Polym Sci, vol. 133, 2016, pp. 44103.

Bassett, et al., "Dual-functional, aromatic, epoxy-methacrylate monomers from bio-based feedstocks and their respective epoxy-functional thermoplastics", J. Polym. Sci., vol. 58, 2020, pp. 673-682.

Fache, et al., "Vanillin, a promising biobased building-block for monomer synthesis", Green Chem, vol. 16, 2014, pp. 1987-1998.

Fei, et al., "Synthesis of photosensitive poly(methyl methacrylate-co-glycidyl methacrylate) for optical waveguide devices", Applied Physics A, vol. 100, 2010, pp. 409-414.

Harvey, et al., "Synthesis and characterization of a renewable cyanate ester/polycarbonate network derived from eugenol", Polymer, vol. 55, 2014, pp. 5073-5079.

Hernandez, et al., "Synthesis and Characterization of Bio-based Epoxy Resins Derived from Vanillyl Alcohol", ACS Sustainable Chemistry & Engineering, vol. 4, 2016, pp. 4328-4339.

Jiang, et al., "Synthesis of well-defined glycidyl methacrylate based block copolymers with self-activation and self-initiation behaviors via ambient temperature atom transfer radical polymerization", Journal of Polymer Science Part A: Polymer Chemistry, vol. 45, 2007, pp. 2947-2958.

Kim, et al., "A dual-functional monomer having an epoxy and methacrylate group for holographic recording", J Mat Chem, vol. 18, 2008, pp. 4762-4768.

Kumar, et al., "Effect of glycidyl methacrylate (GMA) on the thermal, mechanical and morphological property of biodegradable PLA/PBAT blend and its nanocomposites", Bioresource Technology, vol. 101, 2010, pp. 8406-8415.

Kuroishi, et al., "Synthesis and post-polymerisation modification of an epoxy-functional polycarbonate", Polymer Chemistry, vol. 7, 2016, pp. 7108-7115.

La Scala, et al., "The use of bimodal blends of vinyl ester monomers to improve resin processing and toughen polymer properties", Polymer, vol. 46, 2005, pp. 2908-2921.

Luo, et al., "A thermoplastic/thermoset blend exhibiting thermal mending and reversible adhesion", ACS Appl Mater Interfaces, vol. 1, 2009, pp. 612-620.

Muzammil, et al., "Post-polymerization modification reactions of poly(glycidyl methacrylate)s", RSC Advances, vol. 7, 2017, pp. 55874-55884.

Radhakrishnan, et al., "Thermal Degradation Studies of Polythiophenes Containing Hetero Aromatic Side Chains", International Journal of Thermophysics, vol. 30, 2009, pp. 1074-1087.

Yancey, et al., "Adding free volume to PEG based anhydrous proton conducting electrolytes with bulky copolymers", J Electroanal Chem, vol. 706, 2013, pp. 117-126.

* cited by examiner

*Primary Examiner* — Samantha L Shterengarts
(74) *Attorney, Agent, or Firm* — Saul Ewing LLP; Domingos J. Silva; Dennis Ostrovsky

(57) ABSTRACT

The present invention relates to the unexpected discovery of novel monomer compounds capable of crosslinking interpenetrating polymer networks (IPNs). In certain embodiments, the monomer compounds of the invention each comprise at least one methacrylate functionality capable of forming polymeric bonds with other methacrylate and vinyl functionalities, and at least one epoxide functionality capable of forming polymeric bonds with epoxide functionalities, amine functionalities, and/or reactive oxygen species.

10 Claims, 6 Drawing Sheets

| Monomer | $T_m$ (°C) | Enthalpy of Melting (kJ mol$^{-1}$) |
|---|---|---|
| VAEM | 81 | 35.77 |
| SAEM | 73 | 33.46 |
| GDEM | 65 | 32.38 |

EPOXY-(METH)ACRYLATE MONOMERS AND POLYMERS AND METHODS OF MAKING AND USING THE SAME

CROSS-REFERENCE TO RELATED APPLICATIONS

This application claims priority under 35 U.S.C. § 119(e) to U.S. Provisional Patent Application No. 62/718,007, filed Aug. 13, 2018, the contents of which are incorporated by reference herein in their entirety.

STATEMENT REGARDING FEDERALLY SPONSORED RESEARCH OR DEVELOPMENT

This invention was made with government support under grant numbers W911NF-14-2-0086 and W911NF-16-2-0225 awarded by the U.S. Army Research Laboratory. The government has certain rights in the invention.

BACKGROUND OF THE INVENTION

Interpenetrating polymer networks (IPNs) are made up of two or more polymer systems, with at least one of the systems synthesized in the presence of the other. In thermosets, dual cure mechanisms can be adopted to create such systems in-situ. For example, monomers capable of polymerizing by free radical chain polymerization can be mixed with step-growth epoxy/amine systems and then reacted. If the cure reactions occur simultaneously, a simultaneous IPN is formed. If one set of monomers can be made to react before the other, a sequential IPN is formed.

In-situ sequential IPNs have been demonstrated successfully for tool-free processing of composites using radiation (EB/UV) curing methods. For example, epoxy-amine systems comprised of bisphenol A diglycidyl ether (DGEBA) and the cycloaliphatic diamine such as 4,4'-diaminodicyclohexylmethane (PACM) can be reacted fully in the presence of methacrylate monomers at temperatures below 50° C. to form a swollen network (C-Stage, a fully cured resin or cured to the maximum extent). In a subsequent step, heat or irradiation can be used to polymerize the methacrylate monomers, such as hexanediol dimethacrylate (HDDMA), forming an IPN with a high glass transition temperature ($T_g$). IPNs can be linked by adding monomers that contain functionality from both systems (network couplers), and this results in cured materials with significantly higher crosslink density and $T_g$.

A commonly used monomer containing functionality capable of linking both systems is glycidyl methacrylate (GMA). GMA contains both a methacrylate moiety and an epoxide moiety, allowing it to react with two kinds of polymer systems under dual curing conditions. GMA can be used as a co-monomer is a wide variety of applications including automotive coatings, powder coatings, radiation curable coatings, waterborne coatings and resins, protective finishes, appliance and hardware finishes, adhesives, electrical laminates, and plastic modifiers. However, GMA is a liquid at room temperature and can volatilize under curing conditions. Additionally, due to the presence of only a simple methylene link between the methacrylate and epoxide functionalities, GMA is a limited platform for modification as the structure does not allow for the addition of functionalities that can alter and tune the properties of the resulting polymers.

Known benefits of IPN resin systems include: (i) improved fracture toughness, (ii) greatly reduced cure shrinkage relative to pure free radical cured systems, (iii) reduced residual stresses, and (iv) facile bonding of C-stage parts because of the unreacted second phase.

There are currently several technologies available describing the use of UV light to energize thermoset reactions (e.g., (meth)acrylates). Stereolithographic (SLA) methods are used over other techniques when resins have significantly low viscosities that prevent accurate deposition. UV curable liquid based systems have the disadvantage that large changes in volume during curing, known as "shrinkage", cause undesirable stresses in the part. These undesirable stresses can lead to curling of the part and warpage of dimensions. The key to successful printing via these techniques is thus a careful tuning of the $T_g$, viscosity/modulus, density as a function of cure time and temperature, and toughness/hardness balance.

There remains a need in the art for IPNs comprising novel network coupling monomers. In certain embodiments, the novel network coupling monomers should impart desirable properties to the IPN, including structure rigidity, tunable $T_g$, low toxicity, and/or tunable solubility. The present invention fulfills these needs.

BRIEF DESCRIPTION OF THE DRAWINGS

For the purpose of illustrating the invention, depicted in the drawings are certain embodiments of the invention. However, the invention is not limited to the precise arrangements and instrumentalities of the embodiments depicted in the drawings.

In FIG. 2A, the DGEBA was polymerized using 4,4' diaminodicyclohexyl methane (Amicure PACM) in stoichiometric amounts, and EGDMA was polymerized with 35 wt % (based on mass of EGDMA) styrene and cured with 1.5 wt % Trigonox 239 as the free radical initiator. In FIG. 2B, the DGEBA and the epoxide moiety on VAEM were polymerized using 4,4' diaminodicyclohexyl methane (Amicure PACM) in stoichiometric amounts, and the EGDMA and the methacrylate moiety on VAEM were polymerized with 35 wt % (Based on mass of EGDMA) styrene and cured with 1.5 wt % Trigonox 239 as the free radical initiator. The material shown in FIG. 2A exhibited phase separation between the two polymers, while the material shown in FIG. 2B did not, due to the crosslinking between the polymers by the dual functional VAEM.

DETAILED DESCRIPTION OF THE INVENTION

Figure 2B:
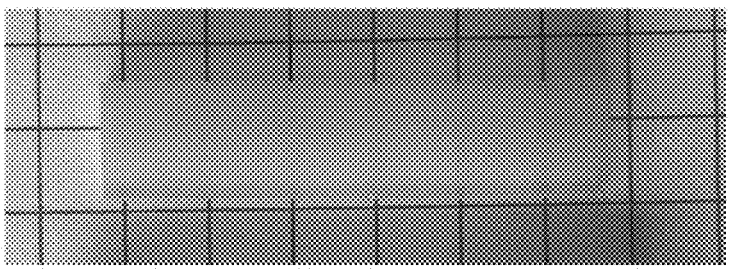
FIGS. 2A-2B are photographs of thermoset interpenetrating polymer networks (IPN) made of bisphenol A diglycidyl ether (DGEBA) and ethylene glycol dimethacrylate (EGDMA) in equimolar amounts (FIG. 2A) and bisphenol A diglycidyl ether (DGEBA) and ethylene glycol dimethacrylate (EGDMA) in equimolar amounts, and VAEM in the amount of 25 mol % (based on the molar quantity of DGEBA) (FIG. 2B).
Figure 2A:
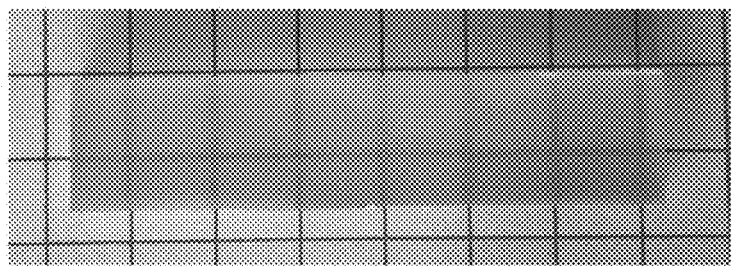
Figure 1:
FIG. 1 is a photograph of vials containing homopolymers of the invention, poly(4-(oxiran-2-ylmethoxy)benzyl methacrylate) (GDEM) and poly(3-methoxy-4-(oxiran-2-ylmethoxy)benzyl methacrylate) (VAEM), as well as prior art polymer poly(glycidyl methacrylate) (GM).
Figure 3B:
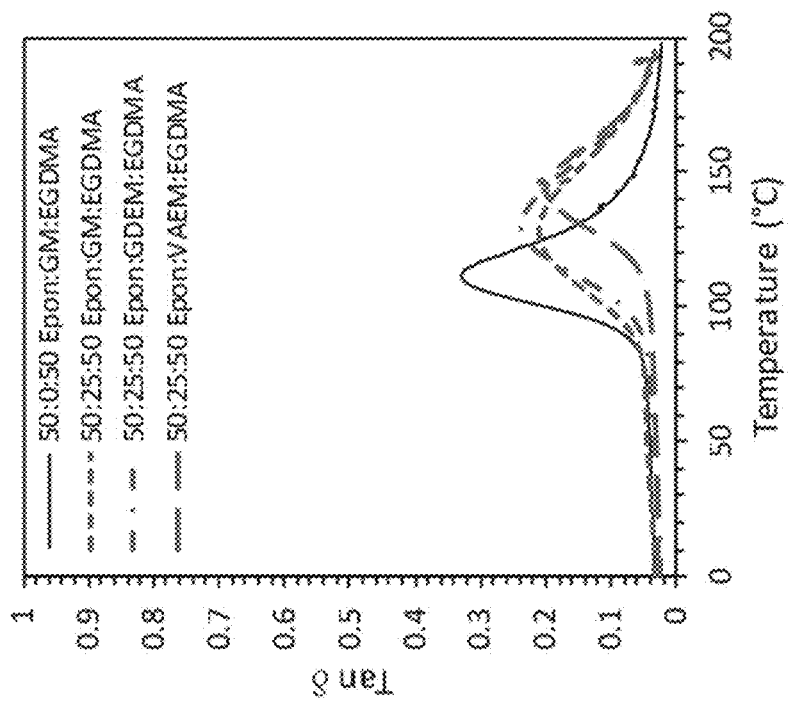
FIGS. 3A-3B are graphs showing dynamic mechanical analysis of a non-crosslinked polymer system, an IPN crosslinked with prior art monomer glycidyl methacrylate, and two IPNs crosslinked with novel monomers 4-(oxiran-2-ylmethoxy)benzyl methacrylate (GDEM) and 3-methoxy-4-(oxiran-2-ylmethoxy)benzyl methacrylate (VAEM).
Figure 3A:
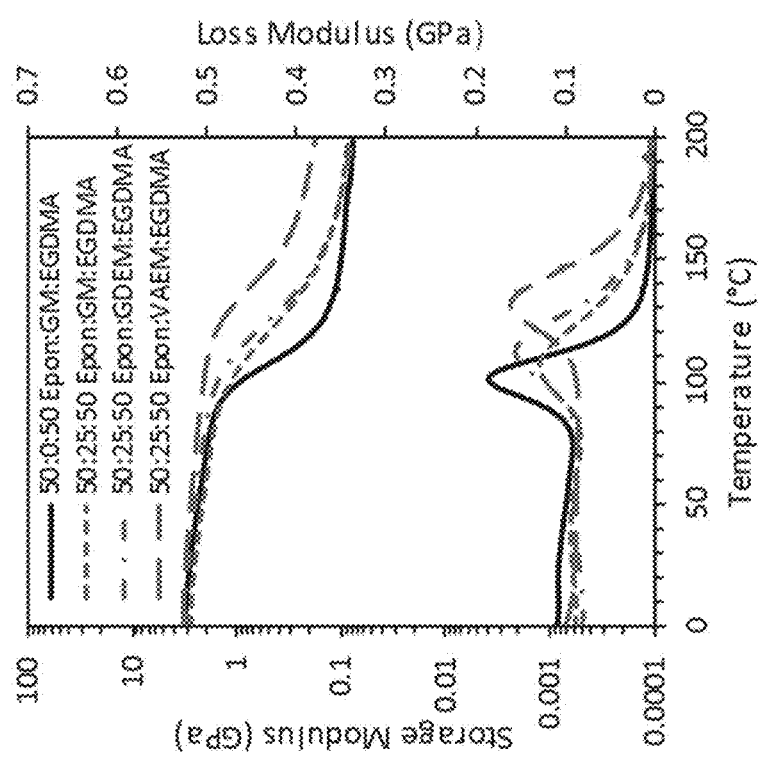

The present invention relates to the unexpected discovery of novel monomer compounds having epoxide functionalities and methacrylate and/or acrylate functionalities. In certain embodiments, the monomers are capable of cross-linking interpenetrating polymer networks (IPNs). In other embodiments, the monomer compounds of the invention comprise at least one methacrylate functionality capable of forming polymeric bonds with other (meth)acrylate and/or vinyl functionalities, and at least one epoxide functionality capable of forming polymeric bonds with epoxide functionalities, amine/anhydride functionalities, and/or reactive oxygen species.

Vanillyl alcohol (VA) and syringyl alcohol (SA), lignin-based aromatic diols and products of lignin depolymerization, and gastrodigenin (GD), a bio-based aromatic diol found in the Chinese *Gastrodia elata* Blume herb and *Coelogossum* orchid, are suitable platform chemicals for the preparation of unique, aromatic GMA compliments due to their natural asymmetry. Additionally, tyrosol is a naturally derived, asymmetric diol found in olive oil and can be recovered from olive oil wastewater streams and is a suitable platform chemical to prepare a GMA compliment. While these compounds have been previously investigated for thermosetting resins, their potential to be transformed into dual functional monomers has not been explored.

The present disclosure details synthesis of aromatic epoxy-methacrylate monomers vanillyl alcohol epoxy-methacrylate (VAEM), syringyl alcohol epoxy-methacrylate (SAEM), gastrodigenin epoxy-methacrylate (GDEM), and tyrosol epoxy-methacrylate (TEM), derived from vanillyl alcohol, syringyl alcohol, gastrodigenin, and tyrosol, respectively. The natural asymmetry and differences in reactivity of the aromatic and aliphatic hydroxyls allow for the facile, selective synthesis of dual functional epoxy-methacrylate monomers.

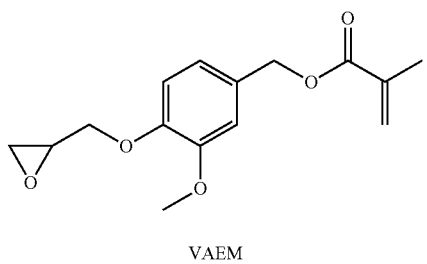

VAEM

-continued

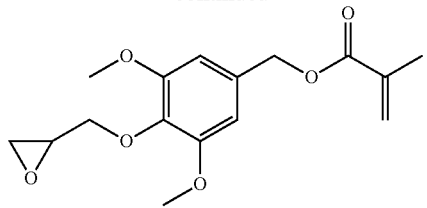

SAEM

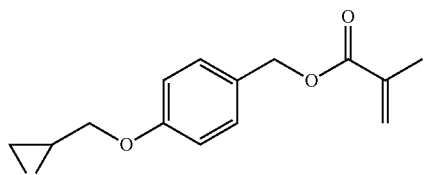

GDEM

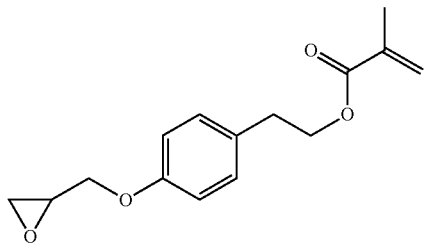

TEM

Additionally, the present disclosure details the preparation of epoxy-functional thermoplastic homopolymers comprised of VAEM, SAEM, GDEM, and TEM. The resultant homopolymers were compared to poly(GMA) to assess the effect of molecular structure on material properties. All polymers were characterized for their molecular weight, thermal stability and $T_g$.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in polymer chemistry and organic chemistry are those well-known and commonly employed in the art. As used herein, the articles "a" and "an" refer to one or to more than one (i.e., to at least one) of the grammatical object of the article. By way of example, "an element" means one element or more than one element.

As used herein, the term "about" will be understood by persons of ordinary skill in the art and will vary to some extent on the context in which it is used. As used herein when referring to a measurable value such as an amount, a concentration, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "(meth)acrylate" refers to a compound comprises at least one methacrylate functionality, at least one acrylate functionality, and any combinations thereof. In certain embodiments, the meth(acrylate) comprises multiple (meth)acrylate functionalities and/or multiple acrylate functionalities, or any combinations thereof.

The term "monomer" refers to any discreet chemical compound of any molecular weight.

As used herein, the term "polymer" refers to a molecule composed of repeating structural units typically connected by covalent chemical bonds. The term "polymer" is also meant to include the terms copolymer and oligomers. In certain embodiments, a polymer comprises a backbone (i.e., the chemical connectivity that defines the central chain of the polymer, including chemical linkages among the various polymerized monomeric units) and a side chain (i.e., the chemical connectivity that extends away from the backbone).

As used herein, the term "polymerization" or "crosslinking" refers to at least one reaction that consumes at least one functional group in a monomeric molecule (or monomer), oligomeric molecule (or oligomer) or polymeric molecule (or polymer), to create at least one chemical linkage between at least two distinct molecules (e.g., intermolecular bond), at least one chemical linkage within the same molecule (e.g., intramolecular bond), or any combinations thereof. A polymerization or crosslinking reaction may consume between about 0% and about 100% of the at least one functional group available in the system. In certain embodiments, polymerization or crosslinking of at least one functional group results in about 100% consumption of the at least one functional group. In other embodiments, polymerization or crosslinking of at least one functional group results in less than about 100% consumption of at least one functional group.

As used herein, the term "reaction condition" refers to a physical treatment, chemical reagent, or combination thereof, which is required or optionally required to promote a reaction. Non-limiting examples of reaction conditions are electromagnetic radiation (such as, but not limited to, visible light and UV light), heat, a catalyst, a chemical reagent (such as, but not limited to, an acid, base, electrophile or nucleophile), and a buffer.

As used herein, the term "alkyl", by itself or as part of another substituent means, unless otherwise stated, a straight or branched chain hydrocarbon having the number of carbon atoms designated (i.e., $C_1$-$C_{15}$ means one to fifteen carbon atoms) and includes straight, branched chain, or cyclic substituent groups. Examples include methyl, ethyl, propyl, isopropyl, butyl, isobutyl, tert-butyl, pentyl, neopentyl, hexyl, cyclopropylmethyl, and dodecanyl. Most preferred is ($C_1$-$C_6$)alkyl, such as, but not limited to, ethyl, methyl, isopropyl, isobutyl, n-pentyl, n-hexyl and cyclopropylmethyl.

As used herein, the term "cycloalkyl", by itself or as part of another substituent means, unless otherwise stated, a cyclic chain hydrocarbon having the number of carbon atoms designated (i.e., $C_3$-$C_6$ means a cyclic group comprising a ring group consisting of three to six carbon atoms) and includes straight, branched chain or cyclic substituent groups. Examples include cyclopropyl, cyclobutyl, cyclopentyl, cyclohexyl, cycloheptyl, and cyclooctyl. Most preferred is ($C_3$-$C_6$)cycloalkyl, such as, but not limited to, cyclopropyl, cyclobutyl, cyclopentyl and cyclohexyl. Examples of polycyclic cycloalkyls include betulin and betulinic acid.

As used herein, the term "alkenyl", employed alone or in combination with other terms, means, unless otherwise stated, a stable mono-unsaturated, di-unsaturated, or tri-unsaturated straight chain or branched chain hydrocarbon group having the stated number of carbon atoms. Examples include vinyl, propenyl (or allyl), crotyl, isopentenyl, butadienyl, 1,3-pentadienyl, 1,4-pentadienyl, and the higher homologs and isomers. A functional group representing an alkene is exemplified by —$CH_2$—CH=$CH_2$.

As used herein, the term "alkynyl", employed alone or in combination with other terms, means, unless otherwise stated, a stable straight chain or branched chain hydrocarbon group with a triple carbon-carbon bond, having the stated number of carbon atoms. Non-limiting examples include ethynyl and propynyl, and the higher homologs and isomers.

As used herein, the term "alkylene" by itself or as part of another substituent means, unless otherwise stated, a straight or branched hydrocarbon group having the number of carbon atoms designated (i.e., $C_1$-$C_{15}$ means one to fifteen carbon atoms) and includes straight, branched chain, or cyclic substituent groups, wherein the group has two open valencies. Examples include methylene, 1,2-ethylene, 1,1-ethylene, 1,1-propylene, 1,2-propylene and 1,3-propylene. Heteroalkylene substituents can be a group consisting of the stated number of carbon atoms and one or more heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group.

As used herein, the term "alkenylene", employed alone or in combination with other terms, means, unless otherwise stated, a stable mono-unsaturated or di-unsaturated straight chain or branched chain hydrocarbon group having the stated number of carbon atoms wherein the group has two open valencies.

As used herein, the term "alkynylene", employed alone or in combination with other terms, means, unless otherwise stated, a stable straight chain or branched chain hydrocarbon group with a triple carbon-carbon bond, having the stated number of carbon atoms wherein the group has two open valencies.

As used herein, the term "substituted alkyl", "substituted cycloalkyl", "substituted alkenyl", "substituted alkynyl", "substituted alkylene", "substituted alkenylene" or "substituted alkynylene" means alkyl, cycloalkyl, alkenyl, alkynyl, alkylene, alkenylene, alkynylene as defined above, substituted by one, two or three substituents selected from the group consisting of $C_1$-$C_{10}$ alkyl, halogen, =O, —OH, alkoxy, tetrahydro-2-H-pyranyl, —$NH_2$, —N($CH_3$)$_2$, (1-methyl-imidazol-2-yl), pyridin-2-yl, pyridin-3-yl, pyridin-4-yl, —C(=O)OH, trifluoromethyl, —C(=O)O($C_1$-$C_4$)alkyl, —C(=O)$NH_2$, —C(=O)NH($C_1$-$C_4$)alkyl, —C(=O)N(($C_1$-$C_4$)alkyl)$_2$, —$SO_2NH_2$, —C(=NH)$NH_2$, and —$NO_2$, preferably containing one or two substituents selected from halogen, —OH, alkoxy, —$NH_2$, trifluoromethyl, —N($CH_3$)$_2$, and —C(=O)OH, more preferably selected from halogen, alkoxy and —OH. Examples of substituted alkyls include, but are not limited to, 2,2-difluoropropyl, 2-carboxycyclopentyl and 3-chloropropyl.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$) alkoxy, such as, but not limited to, ethoxy and methoxy.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2$—$CH_2$—OH, —$CH_2$—$CH_2$—NH—$CH_3$, —$CH_2$—S—$CH_2$—$CH_3$, and —$CH_2CH_2$—S(=O)—$CH_3$. Up to two heteroatoms may be consecutive, such as, for example, —$CH_2$—NH—$OCH_3$, or —$CH_2$—$CH_2$—S—S—$CH_3$.

As used herein, the term "heteroalkenyl" by itself or in combination with another term means, unless otherwise stated, a stable straight or branched chain mono-unsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—$CH_3$, —CH=CH—$CH_2$—OH, —$CH_2$—CH=N—$OCH_3$, —CH=CH—N($CH_3$)—$CH_3$, and —$CH_2$—CH=CH—$CH_2$—SH.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl", employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. Preferred are phenyl and naphthyl, most preferred is phenyl.

As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include isosorbide, isomannide, isoidide, lupeol, indolyl (such as, but not limited to, 3-, 4-, 5-, 6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "substituted" means that an atom or group of atoms has replaced hydrogen as the substituent attached to another group.

For aryl, aryl-($C_1$-$C_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two. In yet another embodiment, the substituents are independently selected from the group consisting of $C_{1-6}$ alkyl, —OH, $C_{1-6}$ alkoxy, halo, amino, acetamido and nitro. As used herein, where a substituent is an alkyl or alkoxy group, the carbon chain may be branched, straight or cyclic, with straight being preferred.

"Instructional material" as that term is used herein includes a publication, a recording, a diagram, or any other medium of expression that can be used to communicate the usefulness of the composition and/or compound of the invention in a kit. The instructional material of the kit may, for example, be affixed to a container that contains the compound and/or composition of the invention or be shipped together with a container that contains the compound and/or composition.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compounds and Compositions

In certain embodiments, the invention includes a monomer of Formula (I):

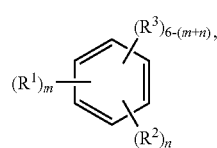

wherein:

$R^1$ is

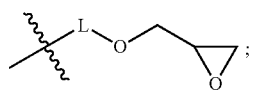

$R^2$ is

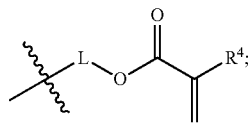

each instance of $R^3$ is independently selected from the group consisting of H, optionally substituted $C_1$-$C_6$ alkyl, and optionally substituted $C_1$-$C_6$ alkoxy;

each instance of $R^4$ is independently selected from the group consisting of H and $CH_3$;

each instance of L is independently selected from the group consisting of a bond, $C_1$-$C_{10}$ alkylene and $C_1$-$C_{10}$ alkenylene; and m is 1, 2, 3, 4 or 5, and n is 1, 2, 3, 4 or 5, such that (m+n) is equal to or less than 6.

In certain embodiments, (m+n) is equal to or less than 5.

In certain embodiments, (m+n) is equal to or less than 4.

In certain embodiments, (m+n) is equal to or less than 3.

In certain embodiments, (m+n) is equal to or less than 2.

In certain embodiments, m and n are both 1.

In certain embodiments where L is a bond in $R^2$, L is selected from the group consisting of $C_1$-$C_{10}$ alkylene and $C_1$-$C_{10}$ alkenylene in $R^1$.

In certain embodiments where L is a bond in $R^1$, L is selected from the group consisting of $C_1$-$C_{10}$ alkylene and $C_1$-$C_{10}$ alkenylene in $R^2$.

In certain embodiments, each instance of L is independently selected from the group consisting of a bond, $C_1$-$C_3$ alkylene and $C_1$-$C_3$ alkenylene.

In certain embodiments, the monomer of Formula (I) is a compound selected from the group consisting of:

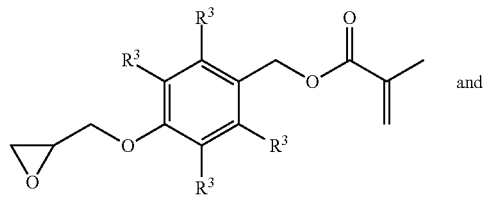 and

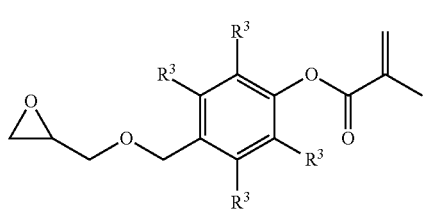

In certain embodiments, the monomer of Formula (I) is a compound selected from the group consisting of:

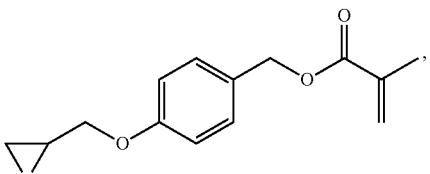

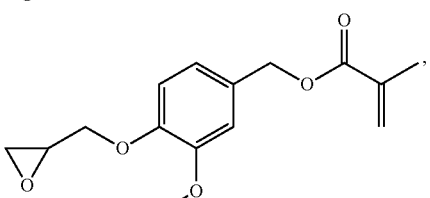

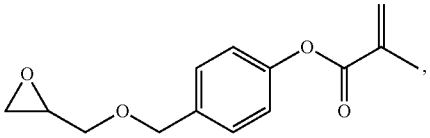

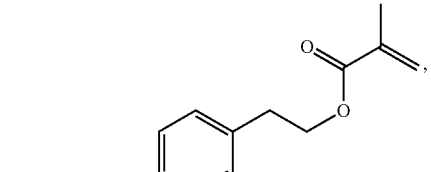

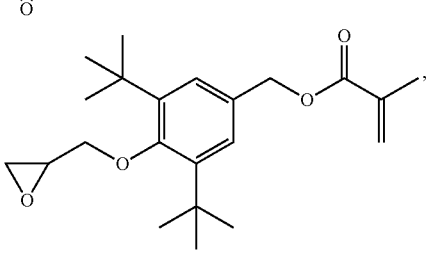

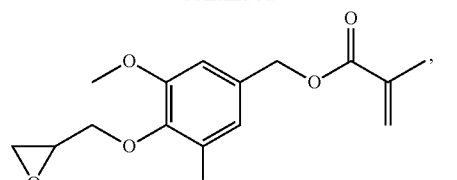
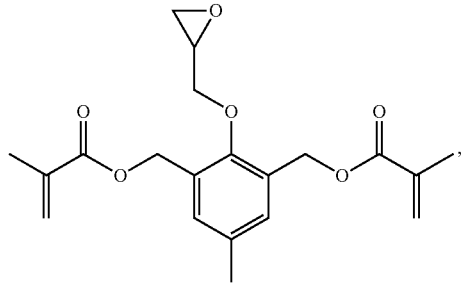
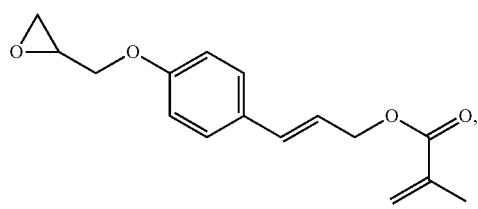
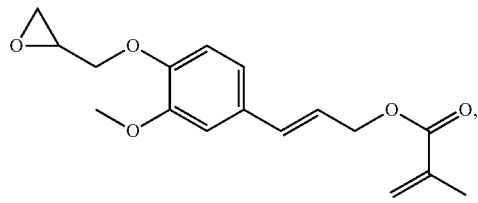
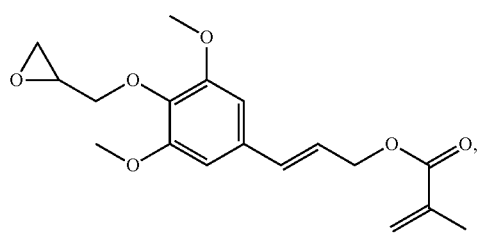
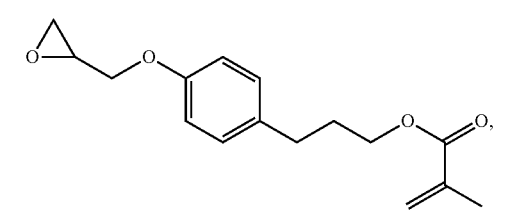
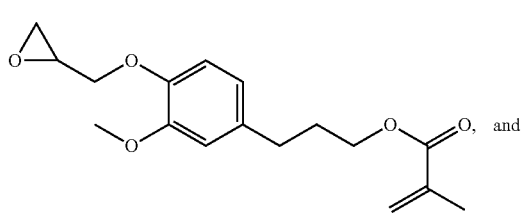
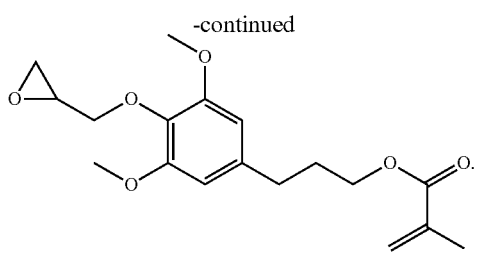
In certain embodiments, the invention includes a monomer of Formula (II):
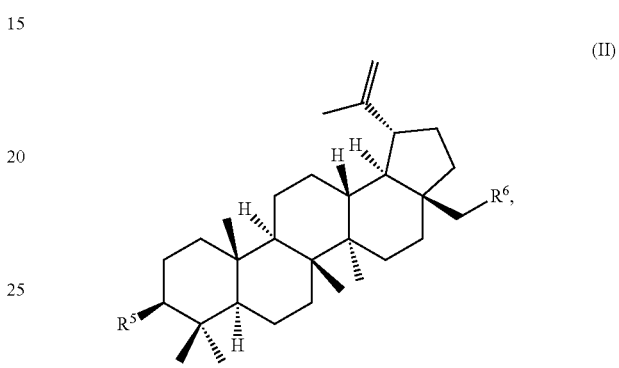
(II)
wherein:
one of $R^5$ and $R^6$ is
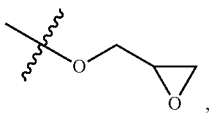
and the other is
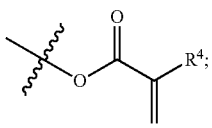
and
each instance of $R^4$ is independently selected from the group consisting of H and $CH_3$.
In certain embodiments, the monomer of Formula (II) is a compound selected from the group consisting of:
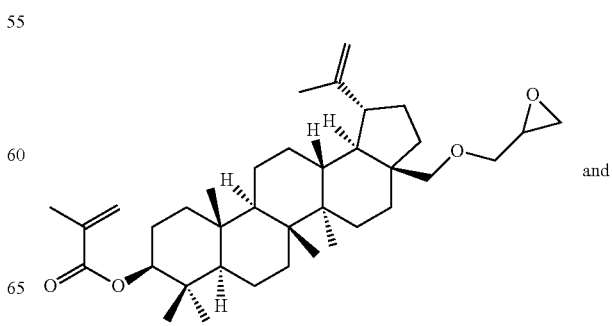
and -continued

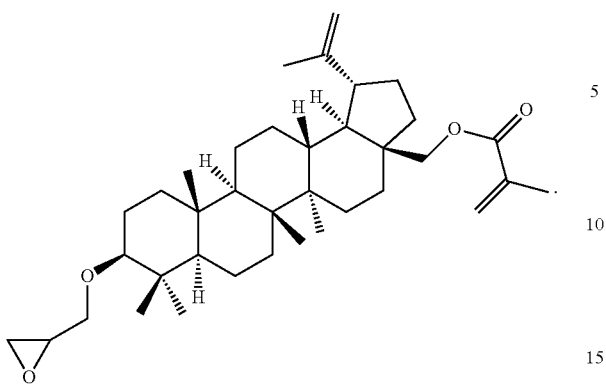

In certain embodiments, the invention includes a monomer of Formula (III):

(III)

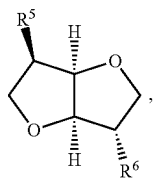

wherein:
one of $R^5$ and $R^6$ is

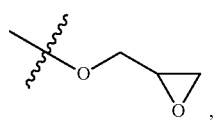 [SMILES: *OCC1CO1]

and the other is

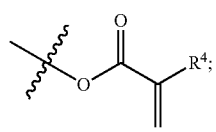

and
each instance of $R^4$ is independently selected from the group consisting of H and $CH_3$.

In certain embodiments, the monomer of Formula (III) is a compound selected from the group consisting of:

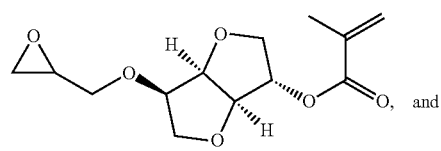

-continued

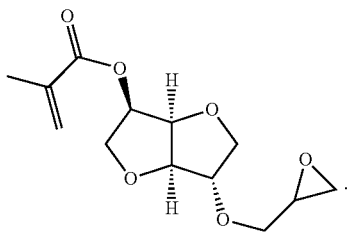

In certain embodiments, the invention provides a composition comprising a monomer of Formula (I). In certain embodiments, the invention provides a composition comprising a monomer of Formula (II). In certain embodiments, the invention provides a composition comprising a monomer of Formula (III).

In certain embodiments, the composition further comprises at least one polymerization initiator. In other embodiments, the composition comprises at least one polymerization initiator selected from the group consisting of photoinitiators, thermal initiators, free radical accelerators, and redox initiators.

In certain embodiments, the photoinitiator is reactive upon exposure to light in the IR (700-1,000,000 nm), visible (400-700 nm) or UV (10-400 nm). In other embodiments, the photoinitiator is a compound belonging to a class selected from the group consisting of acyl phosphines, ketones, diimidazoles, acyl germaniums, thioketones, dithiocarbonates, trithiocarbonates, camphorquinones and camphoramines. In yet other embodiments, the photoinitiator is selected from the group consisting of acetophenone, benzophenone, 2-phenylacetophenone, 2,2-dimethoxy-2-phenylacetophenone, Bis(2,4,6-trimethylbenzoyl)-phenylphosphineoxide, 2-Hydroxy-4'-(2-hydroxyethoxy)-2-methylpropiophenone, 2-methyl-(4-methylthienyl)-2-morpholinyl-1-propan-1-one, Diphenyl(2,4,6-trimethylbenzoyl)phosphine oxide, Ethyl (2,4,6-trimethylbenzoyl) phenyl phosphinate, lithium phenyl-2,4,6-trimethylbenzoylphosphinate,

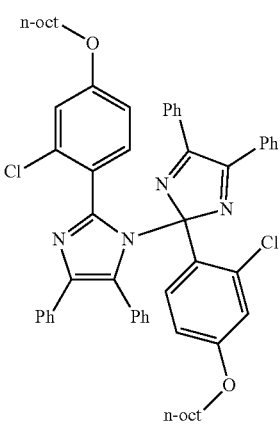

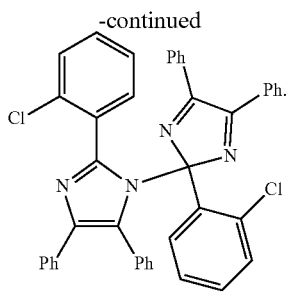

In certain embodiments, the thermal initiator is reactive upon exposure to temperatures of about 30° C. to about 200° C. In other embodiments, the thermal initiator is a compound selected from the group consisting of 4,4'-diaminodicyclohexyl methane, tert-Amyl peroxybenzoate, 4,4-Azobis(4-cyanovaleric acid), 1,1'-Azobis(cyclohexanecarbonitrile), 2,2'-Azobisisobutyronitrile (AIBN), Benzoyl peroxide, 2,2-Bis(tert-butylperoxy)butane, 1,1-Bis(tert-butylperoxy) cyclohexane, 2,5-Bis(tert-butylperoxy)-2,5-dimethylhexane, 2,5-Bis(tert-butylperoxy)-2,5-dimethyl-3-hexyne, Bis(1-(tert-butylperoxy)-1-methylethyl)benzene, 1,1-Bis(tert-butylperoxy)-3,3,5-trimethylcyclohexane, tert-Butyl hydroperoxide, tert-Butyl peracetate, tert-Butyl peroxide, tert-Butyl peroxybenzoate, tert-Butylperoxy isopropyl carbonate, cumene hydroperoxide, methyl ethyl ketone peroxide, cyclohexanone peroxide, dicumyl peroxide, lauroyl peroxide, 2,4-pentanedione peroxide, peracetic acid and potassium persulfate.

In certain embodiments, a suitable free radical accelerator is one or more compounds that includes ferrocene, substituted ferrocene, cobalt naphthalate, cobalt naphthenate, titanocenes, zirconocenes, and the like. Free radical accelerators such as those described in *Stereoselective Polymerization with Single-Site Catalysts,* Lisa S. Baugh and Jo Ann M. Canich (eds.), CRC Press, © 2008, which is herein incorporated by reference in its entirety, that are compatible with any of the monomers described herein, can be used. The free radical accelerator can be stereoselective or non-stereoselective.

In certain embodiments, the redox initiator is one or more compounds selected from the group consisting of sodium iodide/hydrogen peroxide, potassium iodide/hydrogen peroxide, benzoyl peroxide/dimethyaniline, benzoyl peroxide/N,N-dimethyl p-toluidine, benzoyl peroxide/4-N,N-dimethylaminophenethyl alcohol, benzoyl peroxide/ethyl 4-dimethylaminobenzoate, glucose oxidase/oxygen/iron(II) sulfate and copper(II) sulfate/sodium ascorbate.

In certain embodiments, the composition is at least partially polymerized. In certain embodiments, the composition comprises a polymer comprising homo-polymerized monomers of Formula (I). In other embodiments, the composition comprises a polymer comprising homo-polymerized monomers of Formula (II). In yet other embodiments, the composition comprises a polymer comprising homo-polymerized monomers of Formula (III).

In certain embodiments, the composition comprises polymers comprising at least one monomer of the invention, wherein the acrylate/methacrylate functionality is incorporated into the polymeric backbone and the epoxide functionality is left un-polymerized. In other embodiments, the epoxide group can be converted to a different functionality. In yet other embodiments, the epoxide group can be functionalized to form at least one moiety selected from the group consisting of a glycol, a hydroxyamine, a hydroxyester, and a cyclic carbonate. In yet other embodiments, the compounds of the invention can be reacted with carbon dioxide, thereby converting the epoxide functionality to a cyclic carbonate functionality. In certain embodiments, the epoxide functionality allows for an epoxide reactive chemical moiety to be grafted to the polymer.

In certain embodiments, the composition comprises polymers comprising at least one monomer of the invention, wherein the epoxide functionality is incorporated into the polymeric backbone and the acrylate/methacrylate functionality is left un-polymerized. In other embodiments, the acrylate/methacrylate functionality can be converted to a different functionality. In certain embodiments, the acrylate/methacrylate functionality allows for a (meth)acrylate reactive moiety to be grafted to the polymer.

In certain embodiments, the composition further comprises at least one additional compound comprising at least one selected from the group consisting of an epoxide functionality, a methacrylate functionality, a vinyl functionality, an acrylate functionality, an allylic functionality, a cyclic carbonate functionality, a thiol functionality, an amine functionality, an isocyanate functionality, an aldehyde functionality, a hydroxyl functionality, a carboxylic acid functionality, an aniline functionality, an anhydride functionality, and an unsaturated polyester. In other embodiments, the composition further comprises at least one additional compound selected from the group consisting of bisphenol A diglycidyl ether, bisphenol F diglycidyl ether, bisguaiacol diglycidyl ether, novolac epoxies, glycidyl ethers of hydrogenated bisphenols and epoxides, di(cyclohexane epoxidemethyl) ether, epoxy cyclohexyl methyl-epoxy cyclohexane carboxylate, 4,4'-diaminodicyclohexylmethane (PACM), EPIKURE™ W, Jeffamine and other polyetheramines, amidoamines (such as aminopolyamide), diethyltriamine, triethylenetetramine, tetraethylenepentamine, diethylaminopropylamine, trimethylhexamethylenediamine, dipropyltriamine piperidine, N-aminopiperidine, menthanediamine, isophoronediamine, diaminodiphenylsulfone, methylene dianiline, oxydianiline, imidazole, dicyandiamide, ethylene glycol dimethacrylate (EGDMA), hexanediol dimethacrylate (HDDMA), methyl methacrylate (MMA), styrene, glycidyl methacrylate, vinyl esters of bisphenol A diglycidyl ether, bisphenol F diglycidyl ether, glycidyl ethers of hydrogenated bisphenols, novalac epoxies, isobornyl acrylate, isosorbide (meth)acrylate, methacrylated lauric acid, lauryl (meth)acrylate, cyclohexyl methacrylate, furfuryl methacrylate, phthalic anhydride, hexahydrophthalic anhydride, nadic anhydride, nadic methyl anhydride, dodecenylsuccinic anhydride, maleic anhydride, tetrahydrophthalic anhydride, pyromellitic anhydride, trimellitic anhydride, benzophenonetetracraboxylic dianahydride, chlorendic anhydride, hexamethylene diisocyanate, isophorone diisocyanate, methylenediphenyl diisocyanate, and cyclic carbonates (including those based on any of the epoxies listed elsewhere herein, such as bisphenol A cyclic carbonate), any combinations thereof, and any polymers thereof.

In certain embodiments, the composition comprises:
at least one monomer selected from the group consisting of a monomer of Formula (I), a monomer of Formula (II) and a monomer of Formula (III);
at least one monomer capable of forming a first polymer with the at least one monomer of Formulas (I)-(III), wherein the first polymer comprises linkages selected from the group consisting of epoxy linkages, epoxy-amine linkages, epoxy-acrylate linkages, epoxy-methacrylate linkages (Michael addition), and any combinations thereof; and at least one monomer capable of forming a second polymer with the at least one monomer of Formulas (I)-(III), wherein the second polymer comprises linkages selected from the group consisting of acrylate linkages, methacrylate linkages, vinyl linkages, and any combinations thereof.

In certain embodiments, the monomers and compositions are useful for a wide array of applications such as, for example, automotive composites, composites for boating, composites for aircraft, automotive coatings, powder coatings, radiation curable coatings, waterborne coatings resins, industrial & protective finishes, appliance & hardware finishes, adhesives, electrical laminates, hydrogenated LER substitutes, plastic modifiers (PVC, PET, engineering thermoplastics, rubbers), 3D printing resins, SLS printing resins, and additive manufacturing. In other embodiments, the monomers of the invention can be used as additives in the manufacturing of mono-functional oligomers and polymers such that they form an end-cap on the oligomers and polymers, thereby adding dual functionality to the oligomers and polymers.

In certain embodiments, the monomers of the invention are superior to other dual functional monomers known in the art. In other embodiments, the monomers of the invention form polymeric materials having higher glass transition temperatures and higher thermal stabilities than polymers formed by glycidyl methacrylate. In yet other embodiments, the monomers of the invention are solid at room temperature, and are therefore more stable when stored for longer periods of time, whereas dual functional monomers known in the art are liquids at room temperature and are less stable when stored for longer periods of time. Additionally, because the monomers of the invention are solids at room temperature and are not volatile, they possess less of an inhalation risk, and are therefore safer to handle and use than glycidyl methacrylate. In yet other embodiments, the monomers of the invention possess varied functional groups which allow for them to be tuned and modified, altering the properties of the resulting polymeric materials. By comparison, glycidyl methacrylate is not highly functionalizable and cannot be tuned or modified. In yet other embodiments, the monomers of the invention can be synthesized having an acrylate functionality and an epoxide functionality, whereas glycidyl acrylate is unstable.

In certain embodiments, the monomers of the invention are synthesized starting from asymmetric starting materials, such that the addition of the acrylate/methacrylate functional group(s) and the epoxide functional group(s) can be reliably controlled. In other embodiments, the monomers of the invention are synthesized from starting molecules, whereby certain portions of the starting molecules are biased towards substitution with acrylate/methacrylate functional groups(s) and other portions of the starting molecules are biased towards substitution with epoxide functional groups.

Interpenetrating Polymer Network

In certain embodiments, the invention provides an interpenetrating polymer network (IPN), wherein the IPN comprises polymeric units comprising at least one monomer of Formula (I).

In certain embodiments, the composition comprises an IPN comprising a first polymer comprising linkages selected from the group consisting of epoxy linkages, epoxy-amine linkages, epoxy-(meth)acrylate linkages, and any combinations thereof, and a second polymer comprising linkages selected from the group consisting of (meth)acrylate linkages, vinyl linkages, allyl linkages, and any combinations thereof. In other embodiments, the IPN comprises covalent crosslinks between the first polymer and the second polymer, wherein the crosslinks comprise at least one selected from the group consisting of a monomer of Formula (I) and a polymer comprising at least one monomer of Formula (I).

In certain embodiments, the composition comprises an IPN of Formula (IV):

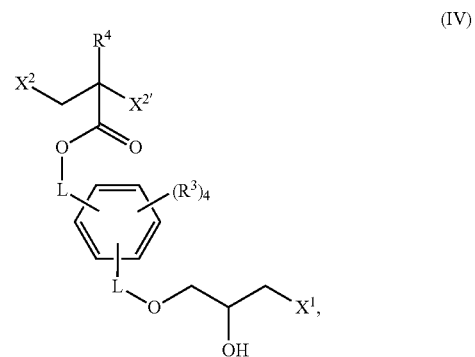

wherein:
$X^1$ is a first polymer comprising linkages selected from the group consisting of epoxy linkages, epoxy-amine linkages, epoxy-(meth)acrylate linkages, and any combinations thereof; and $X^2$ and $X^{2'}$ are independently a second polymer comprising linkages selected from the group consisting of (meth)acrylate linkages, vinyl linkages, and allyl linkages, and any combination thereof; and L, $R^3$ and $R^4$ are as defined elsewhere herein.

In certain embodiments, the composition comprises an IPN of Formula (VA) or Formula (VB):

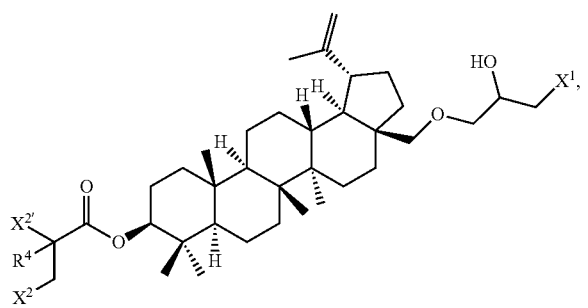

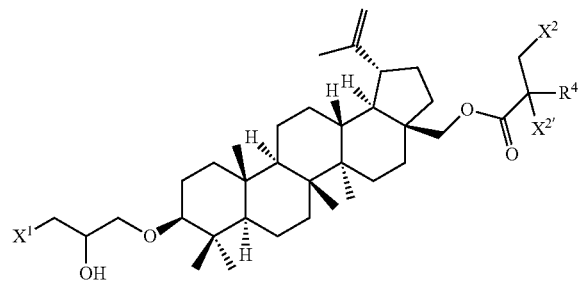

wherein $X^1$, $X^2$, $X^{2'}$, and $R^4$ are as defined elsewhere herein.

In certain embodiments, the composition comprises an IPN of Formula (VI):

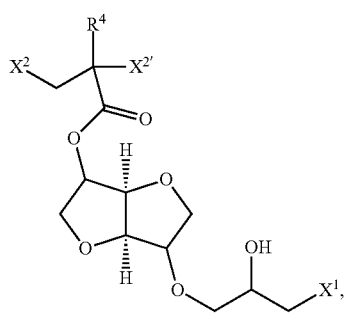

(VI)

wherein $X^1$, $X^2$, $X^{2'}$, and $R^4$ are as defined elsewhere herein.

In certain embodiments, the first polymer comprises at least one additional compound selected from the group consisting of bisphenol A diglycidyl ether, bisphenol F diglycidyl ether, bisguaiacol diglycidyl ether, novolac epoxies, glycidyl ethers of hydrogenated bisphenols and epoxides, di(cyclohexane epoxidemethyl)ether, epoxy cyclohexyl methyl-epoxy cyclohexane carboxylate, 4,4'-diaminodicyclohexylmethane (PACM), EPIKURE™ W, Jeffamine and other polyetheramines, amidoamines (such as aminopolyamide), diethyltriamine, triethylenetetramine, tetraethylenepentamine, diethylaminopropylamine, trimethylhexamethylenediamine, dipropyltriamine piperidine, N-aminopiperidine, menthanediamine, isophoronediamine, diaminodiphenylsulfone, methylene dianiline, oxydianiline and any combinations thereof In certain embodiments, the second polymer comprises at least one monomer selected from the group consisting of ethylene glycol dimethacrylate (EGDMA), hexanediol dimethacrylate (HDDMA), methyl methacrylate (MMA), styrene, glycidyl methacrylate, vinyl esters of bisphenol A diglycidyl ether, bisphenol F diglycidyl ether, glycidyl ethers of hydrogenated bisphenols, and novalac epoxies, isobornyl acrylate, isosorbide (meth)acrylate, methacrylated lauric acid, lauryl (meth)acrylate, cyclohexyl methacrylate, furfuryl methacrylate and any combinations thereof.

In certain embodiments, at least one of the first polymer and the second polymer comprise at least one monomer selected from the group consisting of a monomer of Formula (I), a monomer of Formula (II) and a monomer of Formula (III).

In certain embodiments, the first polymer and the second polymer are formed through different polymerization mechanisms. In one embodiment, the first polymer polymerizes through step-growth polymerization, and the second polymer polymerizes through free radical chain polymerization. In other embodiments, the first polymer polymerizes through cationic epoxy polymerization. In yet other embodiments, the first polymer polymerizes through epoxy-vinyl polymerization (Michael Addition).

In certain embodiments, the IPNs of the invention can be used to make polymer coatings, finishes, adhesives, and/or additive manufacturing resins.

In certain embodiments, the IPNs of the invention are homogeneous IPNs. In other embodiments, the IPNs are substantially transparent. In yet other embodiments, the IPNs are transparent to at least 25% of incident light, 50% of incident light, 75% of incident light, 90% of incident light, or 100% of incident light.

In certain embodiments, the IPNs of the invention have a higher glass transition temperature than analogous IPNs made using glycidyl methacrylate.

Kits

The invention includes a kit comprising a composition of the invention. In certain embodiments, the kit comprises a composition comprising at least one monomer selected from the group consisting of a monomer of Formula (I), a monomer of Formula (II) and a monomer of Formula (III), and instructional material for use thereof. In certain embodiments, the composition further comprises at least one polymerization initiator. In certain embodiments, the composition further comprises at least one additional compound comprising at least one selected from the group consisting of an epoxide functionality, a methacrylate functionality, a vinyl functionality, an acrylate functionality, an allylic functionality, a cyclic carbonate functionality, a thiol functionality, an amine functionality, a carboxylic acid functionality, an aniline functionality, an anhydride functionality, and an unsaturated polyester. In certain embodiments, the composition comprises at least one monomer capable of forming a first polymer comprising linkages selected from the group consisting of epoxy linkages, epoxy-amine linkages, epoxy-(meth)acrylate linkages and any combinations thereof. In other embodiments, the composition comprises at least one monomer capable of forming a second polymer comprising linkages selected from the group consisting of (meth)acrylate linkages, vinyl linkages, allyl linkages, and any combinations thereof.

In certain embodiments, the kit comprises:
a first composition comprising at least one monomer selected from the group consisting of a monomer of Formula (I), a monomer of Formula (II) and a monomer of Formula (III);
a second composition comprising at least one monomer capable of forming with at least one monomer of Formulas (I)-(III) a first polymer comprising linkages selected from the group consisting of epoxy linkages, epoxy-amine linkages, epoxy-acrylate linkages, epoxy-methacrylate linkages, and any combinations thereof;
a third composition comprising at least one monomer capable of forming with at least one monomer of Formula (I) a second polymer comprising linkages selected from the group consisting of acrylate linkages, methacrylate linkages, vinyl linkages, allyl linkages, and any combinations thereof; and
instructional material including instructions for forming an IPN of the invention.

In certain embodiments, at least one of the first composition, second composition and third composition further comprises at least one polymerization initiator.

In certain embodiments, the kit comprises:
a first composition comprising at least one monomer of Formula (IA):

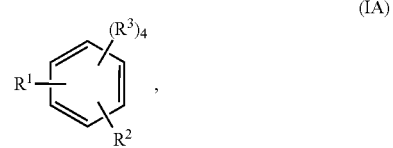

(IA)

wherein in Formula (IA):
R¹ is

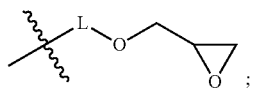

R² is

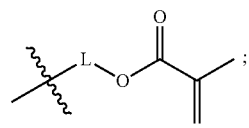

each instance of R³ is independently selected from the group consisting of H, optionally substituted $C_1$-$C_6$ alkyl, and optionally substituted $C_1$-$C_6$ alkoxy; and
each instance of L is independently selected from the group consisting of a bond and methylene;
a second composition comprising at least one monomer capable of forming with at least one monomer of Formula (IA) a first polymer comprising linkages selected from the group consisting of epoxy linkages, epoxy-amine linkages, epoxy-(meth)acrylate linkages, and any combinations thereof;
a third composition comprising at least one monomer capable of forming with at least one monomer of Formula (IA) a second polymer comprising linkages selected from the group consisting of (meth)acrylate linkages, vinyl linkages, allyl linkages, and any combinations thereof; and
instructional material providing instructions for forming an interpenetrating polymer network of Formula (IV) from the first, second, and third compositions.

In certain embodiments, the kit comprises:
a first composition comprising at least one monomer of Formula (II);
a second composition comprising at least one monomer capable of forming with at least one monomer of Formula (II) a first polymer comprising linkages selected from the group consisting of epoxy linkages, epoxy-amine linkages, epoxy-(meth)acrylate linkages, and any combinations thereof;
a third composition comprising at least one monomer capable of forming with at least one monomer of Formula (II) a second polymer comprising linkages selected from the group consisting of (meth)acrylate linkages, vinyl linkages, allyl linkages, and any combinations thereof; and
instructional material providing instructions for forming an interpenetrating polymer network of Formula (VA) or (VB) from the first, second, and third compositions.

In certain embodiments, the kit comprises:
a first composition comprising at least one monomer of Formula (III);
a second composition comprising at least one monomer capable of forming with at least one monomer of Formula (III) a first polymer comprising linkages selected from the group consisting of epoxy linkages, epoxy-amine linkages, epoxy-(meth)acrylate linkages, and any combinations thereof;
a third composition comprising at least one monomer capable of forming with at least one monomer of Formula (III) a second polymer comprising linkages selected from the group consisting of (meth)acrylate linkages, vinyl linkages, allyl linkages, and any combinations thereof; and
instructional material providing instructions for forming an interpenetrating polymer network of Formula (VI) from the first, second, and third compositions.

In certain embodiments, the first composition, the second composition and the third composition are packaged in separate containers. In other embodiments, any combinations of the first composition, the second composition and the third composition are packaged together in the same container and/or are mixed together. In yet other embodiments, at least one of the first composition, the second composition, and the third composition further comprise at least one polymerization initiator.

In certain embodiments, the kit further comprises a light source capable of producing light sufficient to activate a photo polymerization initiator. In other embodiments, the kit further comprises a light source capable of emitting light in the IR (700-1,000,000 nm), visible (400-700 nm) or UV (10-400 nm) ranges. In yet other embodiments, the kit further comprises a heat source capable of producing heat sufficient to activate a thermal polymerization initiator. In other embodiments, the kit further comprises a heat source capable of heating a composition of the invention to a temperature of about 30° C. to about 200° C.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions (e.g., nitrogen atmosphere), and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials

Unless described otherwise, the materials used in the experiments were obtained from commercial sources or obtained by methods known in the art, and used without further purification.

Epichlorohydrin (99%), gastrodigenin (4-hydroxybenzyl alcohol, 97%), dichloromethane (DCM, 99.6%), vanillyl alcohol (4-hydroxy-3-methoxybenzyl alcohol, 99%) and chloroform-d (CDCl$_3$, 99.8 atom % d) were purchased from Acros Organics. Ethyl acetate (99.9%), hexanes (99.9%), methanol (99.8%), tetrahydrofuran (Optima THF, 99.9%) and triethylamine (TEA, 99%) were purchased from Fisher Scientific. Syringyl alcohol [(4-(3-hydroxyprop-1-enyl)-2,6-dimethoxyphenol, 99%] and methacryloyl chloride (97%) were purchased from Alfa Aesar. Tyrosol [2-(4-Hydroxyphenol] ethanol, 98%), N,N-Dimethylformamide (DMF, 99.8%), benzyltriethylammonium chloride (TEBAC, 99%), and poly(GMA) (M$_n$=10,000-20,000 Da) were purchased from Sigma Aldrich. 2,2'-Azobis(2-methylpropinitrile) (AIBN, 95%) was purchased from AstaTech. Compressed nitrogen (N$_2$, 99.998%), and compressed argon (Ar, 99.999%) were purchased from Airgas. Sodium hydroxide was purchased from VWR. All chemicals mentioned above were used without further purification.

Characterization of Monomers and Homopolymers All molecules and homopolymers synthesized in this work were characterized by $^1$H-NMR (400.15 MHz, 32 scans at 298 K). Additionally, all new molecules were characterized by $^{13}$C NMR (111 MHz, 512 scans at 298 K) using a Varian 400 MHz FT-NMR Spectrometer. High resolution mass spectrometry (TOF FIRMS) was used to determine the exact mass of the molecules. Spectra were recorded on a Waters Xevo G2 XS QToF Mass Spectrometer.

The melting points of the monomers were measured using a TA Instruments Differential Scanning calorimeter (DSC) 2500. Approximately 10 mg of sample was placed within a Tzero pan with a Tzero Hermetic lid and heated from 30° C. at a rate of 10° C. min$^{-1}$ in a N$_2$ atmosphere. Based on characterization methods, all final dual functional monomers were determined to be >98% pure.

The number-average molecular weight (M$_n$), weight-average molecular weight (M$_w$), and dispersity (Ð) were obtained on a Waters Acquity Advanced Polymer Chromatography (APC) instrument with THF as the eluent (0.6 mL min$^{-1}$), using polystyrene standards with M$_n$ of 537,000 Da (Ð=1.03), 59,300 Da (Ð=1.05), and 8,650 Da (Ð=1.03) as a reference.

Glass transition temperatures (T$_g$)s of all polymers were determined using a TA Instruments DSC 2500. A Tzero aluminium pan was loaded with 3-6 mg of sample and sealed with a Tzero Hermetic lid. Three heating and cooling cycles were performed at a rate of 10° C. min$^{-1}$ under continuous N$_2$ flow (50 mL min$^{-1}$) with a temperature ramp range of 0-150° C. The second and third cycles had no significant changes. The T$_g$ was determined as the midpoint of the inflection in the second heating cycle.

The thermal degradation properties of the polymers (initial decomposition temperature (IDT), temperature at 50% weight loss (T$_{50\%}$), temperature at maximum degradation rate (T$_{max}$), and char content were characterized using a TA Instruments Discovery Thermogravimetric Analyzer (TGA) 550. A powdered sample of 4-6 mg of each polymer was loaded into platinum pans and heated a rate of 10° C. min$^{-1}$ to 700° C. in either a N$_2$ or air atmosphere (40 mL min$^{-1}$ balance gas flow rate and 25 mL min$^{-1}$ sample gas flow rate). Each polymer was run in triplicate for oxidative (air) and N$_2$ environments.

General Comments about Monomer Synthesis & Characterization

VA, SA, GD, and tyrosol bear aromatic and aliphatic hydroxyls, with the aromatic hydroxyl being more acidic and more reactive towards epichlorohydrin. Synthesis of monoglycidyl ethers of these compounds as intermediate building blocks for other modifications have not been carried out. The synthesis for all monoglycidyl ethers were adapted from literature (Fache, et al., 2014, Green Chem. 16(4):1987-1998), whereby the monoepoxidized intermediate is produced as the major product, in which the aliphatic hydroxyl is unreacted. The monoglycidyl ethers of VA, SA, and GD exhibit a characteristic singlet at 4.6 ppm in CDCl$_3$, confirming the aliphatic methylene is adjacent to an unreacted hydroxyl. The monoglycidyl ether of tyrosol exhibits a similar characteristic peak, a triplet at 3.8 ppm in CDCl$_3$, indicating that the aliphatic hydroxyl is unreacted. The unreacted aliphatic hydroxyl was then esterified via methacryloyl chloride to prepare the dual functional monomers VAEM, SAEM, GDEM, and TEM. Excess triethylamine was utilized in the synthesis to ensure rapid trapping of hydrochloric acid that is formed during the reaction to prevent epoxy ring opening. Esterification of the aliphatic hydroxyl is confirmed via $^1$H-NMR, as the aliphatic methylene protons shift to 5.1 ppm in CDCl$_3$ for the synthesis of VAEM, SAEM, and GDEM. Similarly, esterification of the aliphatic hydroxyl is confirmed in the synthesis of TEM, as the protons adjacent to the aliphatic hydroxyl shift to 4.3 ppm in CDCl$_3$. The general synthesis schematic for the production of the dual functional monomers is shown in Scheme 1.

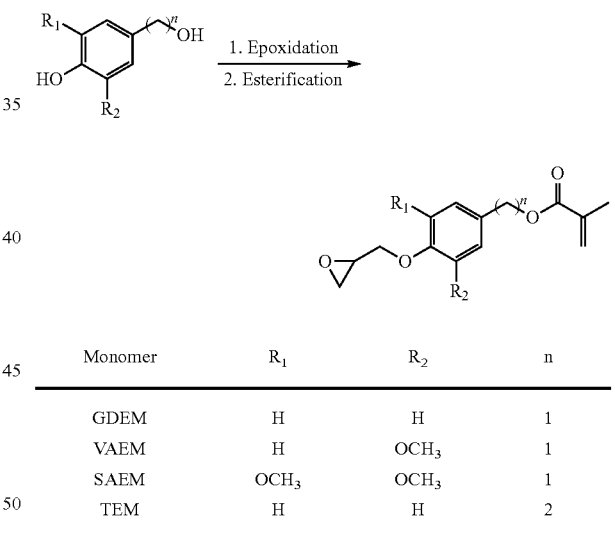

Scheme 1. General synthesis route for the preparation of dual functional monomers.

| Monomer | R$_1$ | R$_2$ | n |
|---|---|---|---|
| GDEM | H | H | 1 |
| VAEM | H | OCH$_3$ | 1 |
| SAEM | OCH$_3$ | OCH$_3$ | 1 |
| TEM | H | H | 2 |

VAEM, SAEM, and GDEM are similar in structure: VAEM bears a methoxy moiety ortho to the glycidyl ether, SAEM bears two methoxy moieties that are both ortho to the glycidyl ether, and GDEM does not bear any aromatic substituents. TEM and GDEM are also similar in structure, with the only difference being that TEM bears an ethylene spacer between the aromatic ring and methacrylate whereas GDEM bears a methylene spacer. These monomers have both methacrylate and epoxy functionalities similar to GMA, yet contain aromaticity at the core of the molecule, which can enhance material properties, such as thermal stability and hydrophobicity. Additionally, the synthesized monomers are all solids at room temperature, increasing storage stability and reducing volatility relative to GMA.

Synthesis of 4-(oxiran-2-ylmethoxy)benzyl methacrylate (GDEM)

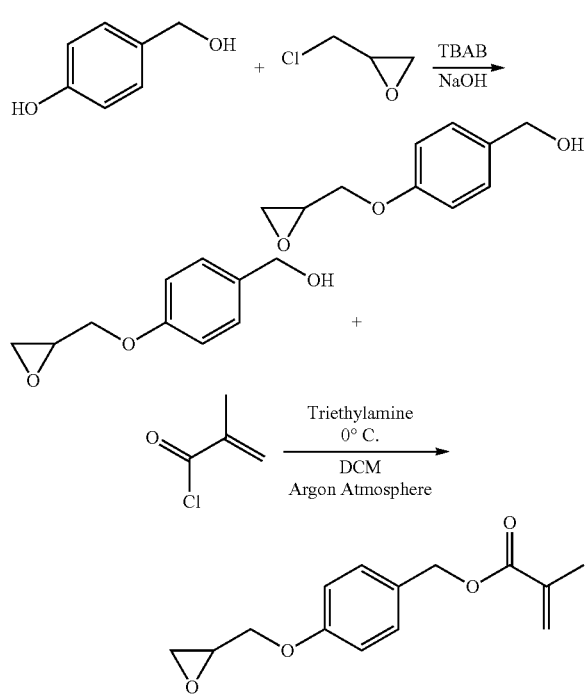

Gastrodigenin (30 g), epichlorohydrin (189.48 mL) and TEBAC (5.50 g) were added to a three-neck round bottom equipped with a mechanical mixer. The reaction mixture was heated to 80° C. for 1 hour. After the 1 hour, the reaction was cooled to room temperature and a mixture of 5 M NaOH (193.3 mL) and TEBAC (5.50 g) was added dropwise. The reaction was then worked up and washed with a solution of equal parts DI water and ethyl acetate. Flash chromatography was used to purify the intermediate product, monoglycidyl ether of gastrodigenin (MGEGD, 60% yield, white powder).

(4-(oxiran-2-ylmethoxy)phenyl)methanol (MGEGD, $C_{10}H_{12}O_3$). White solid, mp. 63-64° C. $^1$H-NMR (CDCl$_3$) δ 2.7 (1H, dd), 2.9 (1H, t), 3.4 (1H, m), 4.0 (1H, dd), 4.2 (1H, dd), 4.6 (2H, s), 6.9 (2H, m), 7.3 (2H, m).

MGEGD (25.49 g) was added to a three-neck round bottom with DCM (42.00 mL) and triethylamine (39.46 mL) in an ice bath with a dropping funnel and an inlet for dry argon gas. Once the contents were cooled to 0° C., a DCM (87.10 mL) and methacryloyl chloride (14.53 mL) solution was added dropwise with constant stirring. After 24 hours, DCM was added to the mixture and then washed once with 2.5 M NaOH solution. The organic phase was isolated, and solvent removed using reduced pressure. The product, gastrodigenin epoxy methacrylate (GDEM, 66% yield, white solid), was further purified using flash chromatography.

4-(oxiran-2-ylmethoxy)benzyl methacrylate (GDEM, $C_{14}H_{16}O_4$). White solid, mp. 63-65° C. $^1$H-NMR (CDCl$_3$) δ 2.0 (3H, t), 2.7 (1H, dd), 2.9 (1H, t), 3.4 (1H, m), 4.0 (1H, dd), 4.2 (1H, dd), 5.1 (2H, s), 5.6 (1H, d), 6.1 (1H, d), 6.9 (2H, m), 7.3 (2H, m). $^{13}$C-NMR (CDCl$_3$): δ 18.3, 44.6, 50.0, 66.1, 68.7, 114.5, 125.6, 128.8, 129.8, 136.2, 158.4, 167.2. HRMS Calculated: 248.1049. Found: 248.1081.

Synthesis of 3-methoxy-4-(oxiran-2-ylmethoxy)benzyl methacrylate (VAEM)

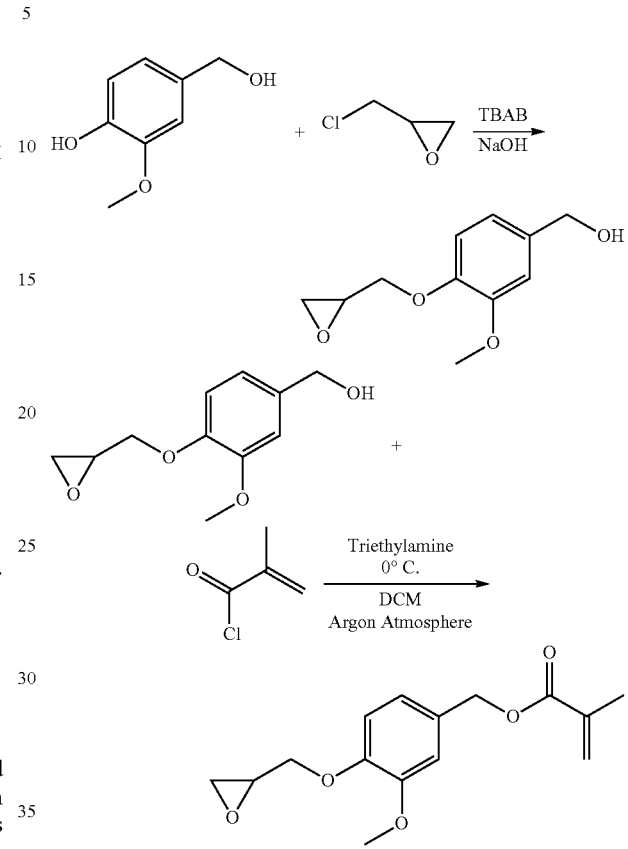

Vanillyl alcohol (5 g), epichlorohydrin (25.43 mL) and TEBAC (0.74 g) were added to a three-neck round bottom equipped with a mechanical mixer. The reaction mixture was heated to 80° C. for 1 hour. After the 1 hour, the reaction was cooled to room temperature and a mixture of 5 M NaOH (25.9 mL) and TEBAC (0.74 g) was added dropwise. The reaction was then worked up and washed with a solution of equal parts DI water and ethyl acetate. Flash chromatography was used to purify the intermediate product, monoglycidyl ether of vanillyl alcohol (MGEVA, 55% yield, white powder).

(3-methoxy-4-(oxiran-2-ylmethoxy)phenyl)methanol (MGEVA, $C_{11}H_{14}O_4$) White solid, mp. 71-73° C. $^1$H-NMR (CDCl$_3$) 2.7 (1H, dd), 2.9 (1H, t), 3.4 (1H, m), 3.9 (3H, s), 4.0 (1H, dd), 4.2 (1H, dd), 4.6 (2H, s), 6.9 (3H, m).

MGEVA (3.726 g) was added to a three-neck round bottom with DCM (5.26 mL) and triethylamine (4.944 mL) in an ice bath with a dropping funnel and an inlet for dry argon gas. Once the contents were cooled to 0° C., a DCM (10.91 mL) and methacryloyl chloride (1.821 mL) solution was added dropwise with constant stirring. After 24 hours, DCM was added to the mixture and then washed once with 2.5 M NaOH solution. The organic phase was isolated, and solvent removed using reduced pressure. The product, vanillyl alcohol epoxy methacrylate (VAEM, 62% yield, white solid), was further purified using flash chromatography.

3-methoxy-4-(oxiran-2-ylmethoxy)benzyl methacrylate (VAEM, $C_{15}H_{18}O_5$). White solid, mp. 79-81° C. $^1$H-NMR (CDCl$_3$) δ 2.0 (3H, t), 2.7 (1H, dd), 2.9 (1H, t), 3.4 (1H, m), 3.9 (3H, s), 4.0 (1H, dd), 4.2 (1H, dd), 5.1 (2H, s), 5.6 (1H, d), 6.1 (1H, d), 6.9(3H, m). $^{13}$C-NMR (CDCl$_3$): δ 18.2, 44.7, 50.0, 55.8, 66.2, 70.1, 112.0, 113.7, 120.8, 125.6, 129.6, 136.1, 147.8, 149.4, 167.1. HRMS Calculated: 278.1154. Found: 278.1172.

Synthesis of 3,5-dimethoxy-4-(oxiran-2-ylmethoxy)benzyl methacrylate (SAEM)

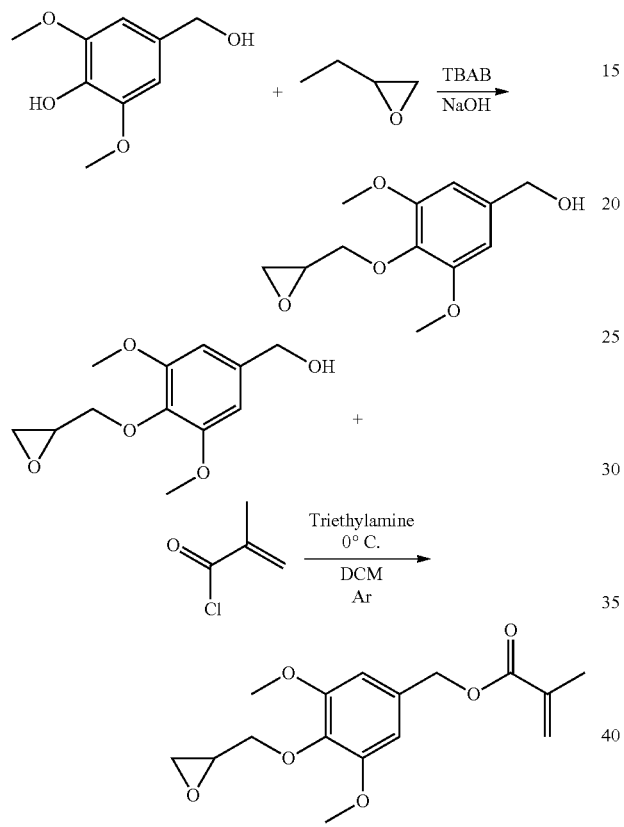

Syringyl alcohol (4 g), epichlorohydrin (17.03 mL) and TEBAC (0.49 g) were added to a three-neck round bottom equipped with a mechanical mixer. The reaction mixture was heated to 80° C. for 1 hour. After the 1 hour, the reaction was cooled to room temperature and a mixture of 5 M NaOH (17.4 mL) and TEBAC (0.49 g) was added dropwise. The reaction was then worked up and washed with a solution of equal parts DI water and ethyl acetate. Flash chromatography was used to purify the intermediate product, mono-glycidyl ether of syringyl alcohol (MGESA, 28% yield, pale yellow liquid).

(3,5-dimethoxy-4-(oxiran-2-ylmethoxy)phenyl)methanol (MGESA, C$_{12}$H$_{16}$O$_5$). Pale yellow liquid. $^1$H-NMR (CDCl$_3$) δ 2.6 (1H, dd), 2.8 (1H, t), 3.4 (1H, m), 3.9 (6 H, s), 4.0 (1H, dd), 4.2 (1H, dd), 4.6 (2H, s), 6.6 (2H, s)

MGESA (1 g) was added to a three-neck round bottom with DCM (1.24 mL) and triethylamine (1.16 mL) in an ice bath with a dropping funnel and an inlet for dry argon gas. Once the contents were cooled to 0° C., a DCM (2.56 mL) and methacryloyl chloride (0.43 mL) solution was added dropwise with constant stirring. After 24 hours, DCM was added to the mixture and then washed once with 2.5 M NaOH solution. The organic phase was isolated, and solvent removed using reduced pressure. The product, syringyl alcohol epoxy methacrylate (SAEM, 48% yield, white solid), was further purified using flash chromatography.

3,5-dimethoxy-4-(oxiran-2-ylmethoxy)benzyl methacrylate (SAEM, C$_{16}$H$_{12}$O$_6$). White solid, mp. 73-75° C. $^1$H-NMR (CDCl$_3$) δ 2.0 (3H, t), 2.6 (1H, dd), 2.8 (1H, t), 3.4 (1H, m), 3.9 (6 H, s), 4.0 (1H, dd), 4.2 (1H, dd), 5.1 (2H, s), 5.6 (1H, d), 6.2 (1H, d), 6.6 (2H, s). $^{13}$C-NMR (CDCl$_3$): δ 18.3, 44.7, 50.5, 56.1, 66.5, 74.1, 105.1, 125.9, 132.0, 136.1, 136.5, 153.2, 167.2. HRMS Calculated: 308.1260. Found: 308.1284.

Synthesis of 4-(oxiran-2-ylmethoxy)phenethyl methacrylate (TEM)

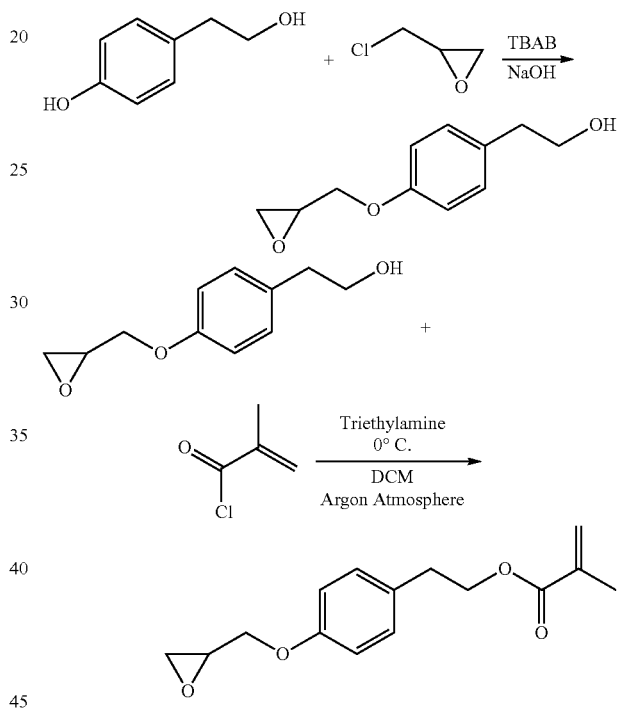

Tyrosol (4 g), epichlorohydrin (22.70 mL) and TEBAC (0.66 g) were added to a three-neck round bottom equipped with a mechanical mixer. The reaction mixture was heated to 80° C. for 1 hour. After the 1 hour, the reaction was cooled to room temperature and a mixture of 5 M NaOH (23.2 mL) and TEBAC (0.66 g) was added dropwise. The reaction was then worked up and washed with a solution of equal parts DI water and ethyl acetate. Flash chromatography was used to purify the intermediate product, mono-glycidyl ether of tyrosol (MGET, 74% yield, white powder).

2-(4-(oxiran-2-ylmethoxy)phenyl)ethan-1-ol (MGET, C$_{11}$H$_{14}$O$_3$). White solid, mp. 60-62° C. $^1$H-NMR (CDCl$_3$) δ 2.7 (1H, dd), 2.8 (2H, t), 2.9 (1H, t), 3.3 (1H, m), 3.8 (2H, q), 3.9 (1H, dd), 4.2 (1H, dd), 6.9 (2H, m), 7.1 (2H, m).

MGET (3.5 g) was added to a three-neck round bottom with DCM (5.35 mL) and triethylamine (5.03 mL) in an ice bath with a dropping funnel and an inlet for dry argon gas. Once the contents were cooled to 0° C., a DCM (11.09 mL) and methacryloyl chloride (1.85 mL) solution was added dropwise with constant stirring. After 24 hours, DCM was added to the mixture and then washed once with 2.5 M NaOH solution. The organic phase was isolated, and solvent removed using reduced pressure. The product tyrosol epoxy methacrylate (TEM, 35% yield, white solid), was further purified using flash chromatography.

4-(oxiran-2-ylmethoxy)phenethyl methacrylate (TEM, $C_{15}H_{18}O_4$). Polymerized before $T_m$. $^1$H-NMR 2.0 (3H, t), 2.7 (1H, dd), 2.9 (3H, m), 3.4 (1H, m), 4.0 (1H, dd), 4.2 (1H, dd), 4.3 (2H, t), 5.5 (1H, d), 6.1 (1H, d), 6.9 (2H, m), 7.2 (2H, m). $^{13}$C-NMR (CDCl$_3$): δ 18.2, 34.1, 44.6, 50.0, 65.2, 68.7, 114.5, 125.3, 129.8, 130.5, 136.2, 157.1, 167.2. HRMS Calculated: 262.1205. Found: 262.1208.

General Comments about Polymer Characterization

Each of the synthesized monomers were individually polymerized in bulk solution polymerizations adapted from the work of Fei, et al., 2010, Applied Physics A 100(2):409-414. The resulting homopolymers were white solids at 25° C. Poly(GMA), a white solid at 25° C., was purchased from Sigma-Aldrich and used as a reference. The structures of the homopolymers aee illustrated in Scheme 2.

Scheme 2. Synthesized epoxy-functional thermoplastics.

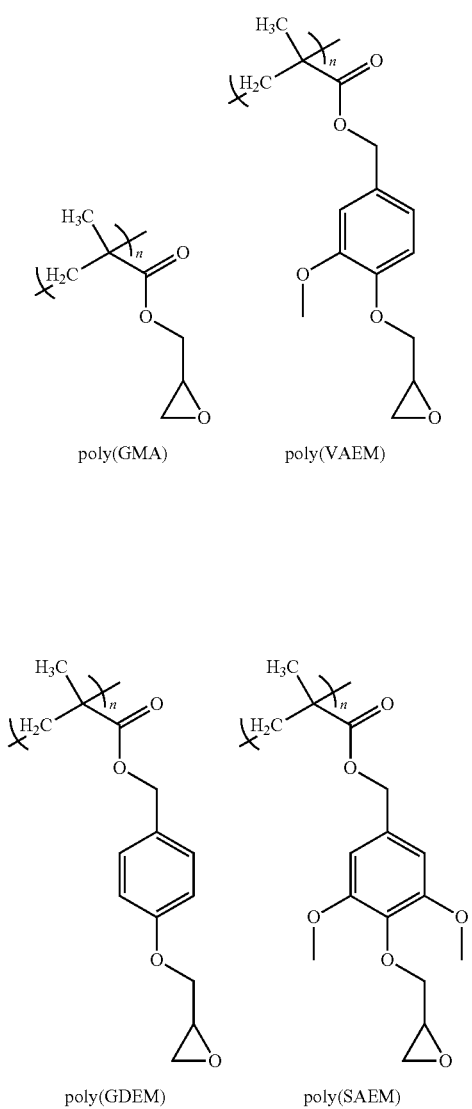

poly(GMA)   poly(VAEM)

poly(GDEM)   poly(SAEM)

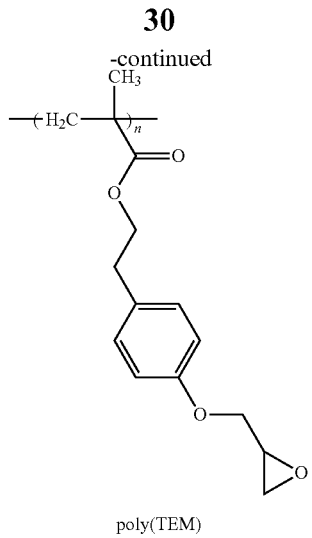

poly(TEM)

The presence of the epoxy group on the pendant chain was confirmed via $^1$H-NMR for each homopolymer. The reference peak of the two hydrogens on the methylene bridge, located at 4.8 ppm on the spectrum, was set to an integration of 2. The protons present on the epoxy are at 3.6 ppm and 2.7-2.7 ppm, respectively. Each epoxy proton peak integrated to approximately 1, indicating the preservation of three protons on the epoxy ring.

The molecular weights and glass transition temperature ($T_g$s) of each polymer were determined using size exclusion chromatography (SEC) and DSC, respectively. All synthesized polymers exhibited $T_g$s within the range of 60-68° C., similar to that of poly(GMA), with the exception of poly (TEM) at 46° C. The similarities in the $T_g$s indicate the methacrylate backbone has a more substantial effect on the $T_g$ than the aromatic ring in the pendant group of the prepared homopolymers. In addition, the methoxy substituents of the poly(VAEM) and poly(SAEM) have minimal impact on $T_g$. However, when considering the additional carbon between the polymer backbone and the aromatic ring present in poly(TEM), the $T_g$ of the homopolymer decreases approximately 20° C. due to the enhanced free rotation in the pendant group.

Figure 4:
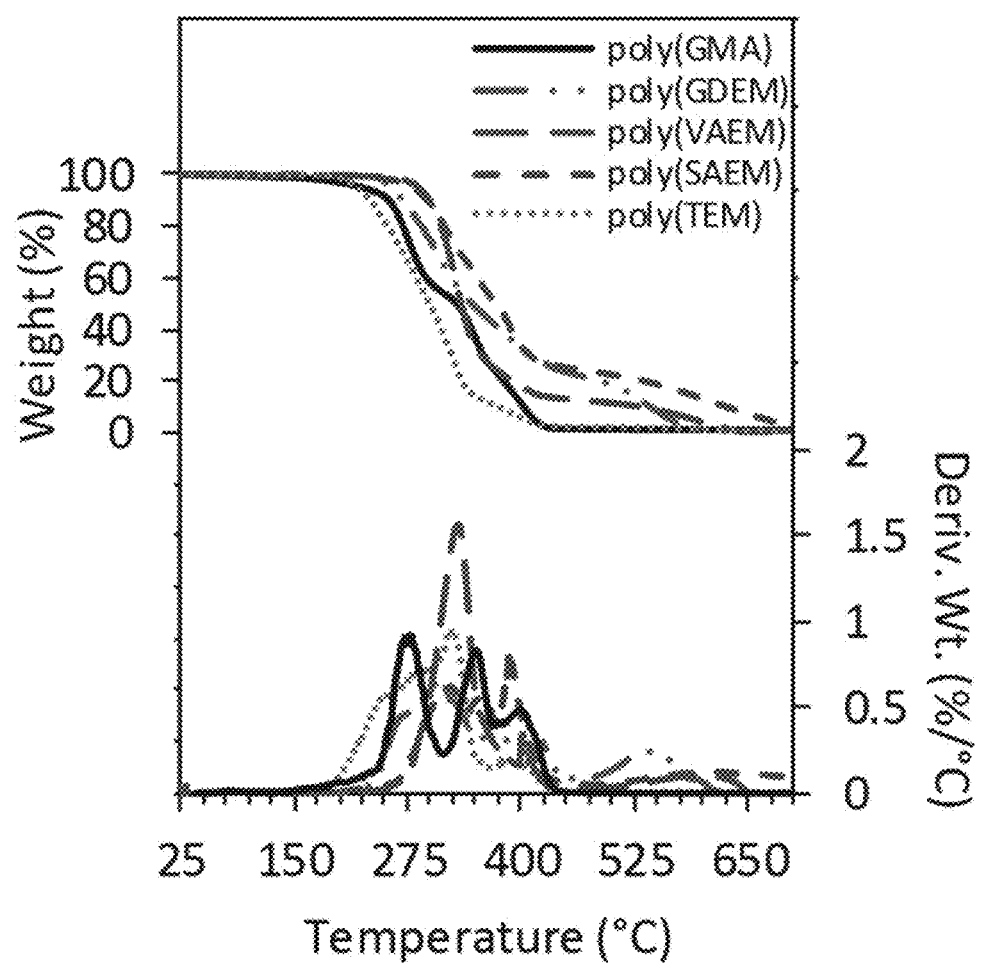
FIG. 4 is a graph showing TGA thermograms and their respective first derivatives of polymers in nitrogen gas.
Figures 5, 6:
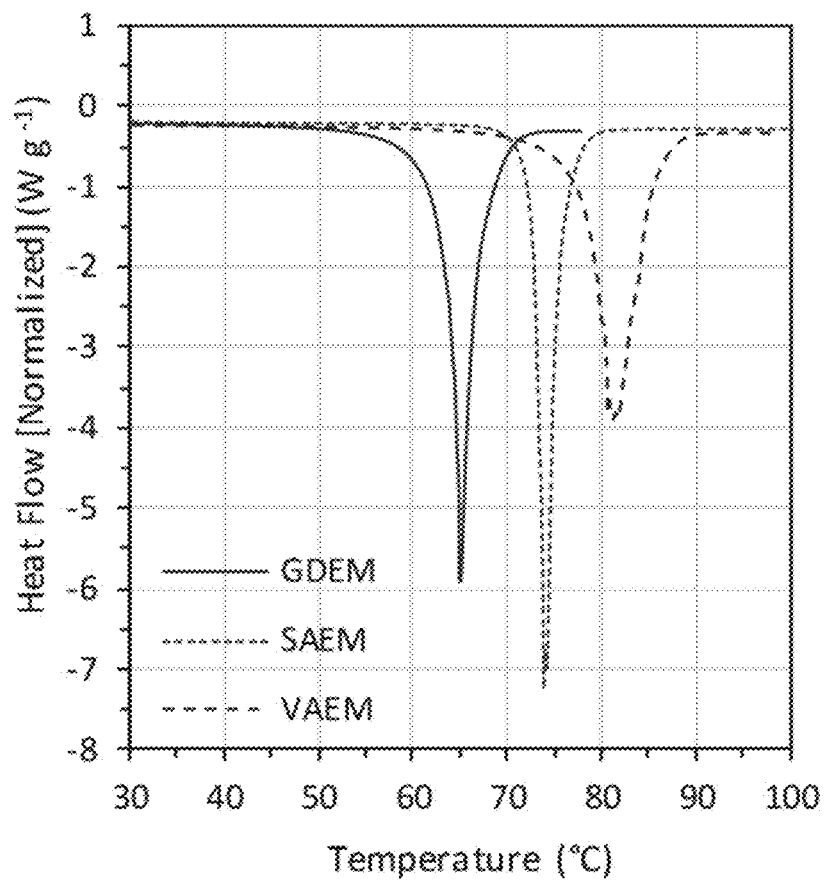
FIG. 5 is a graph illustrating DSC traces of VAEM, SAEM, and GDEM.
FIG. 6 is a table illustrating DSC results, including $T_m$ and enthalpy of melting, for VAEM, SAEM, and GDEM.
Figure 7:
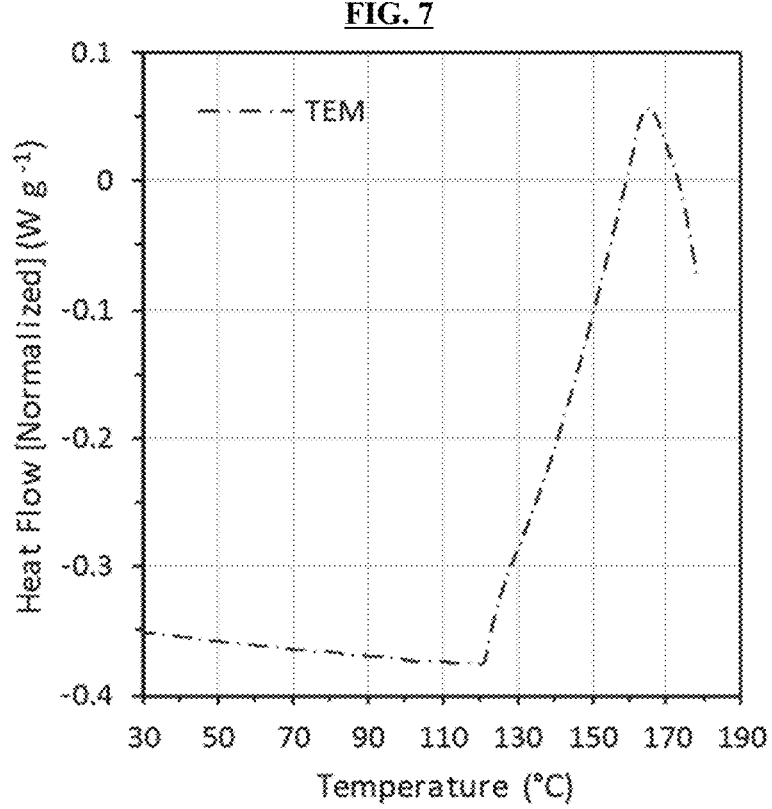
FIG. 7 is a graph illustrating a DSC trace of TEM.
Figure 8:
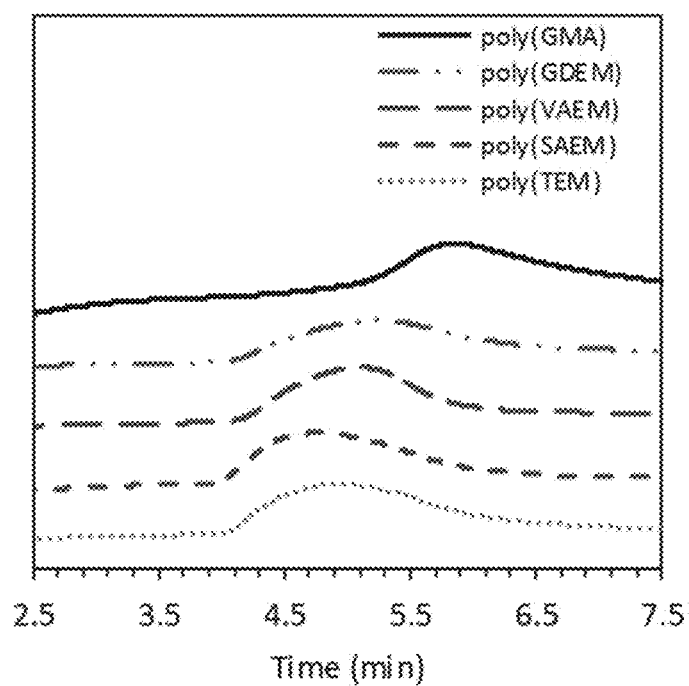
FIG. 8 is a graph illustrating APC plots of the thermoplastic polymers. Vertically offset for clarity.
Figure 9:
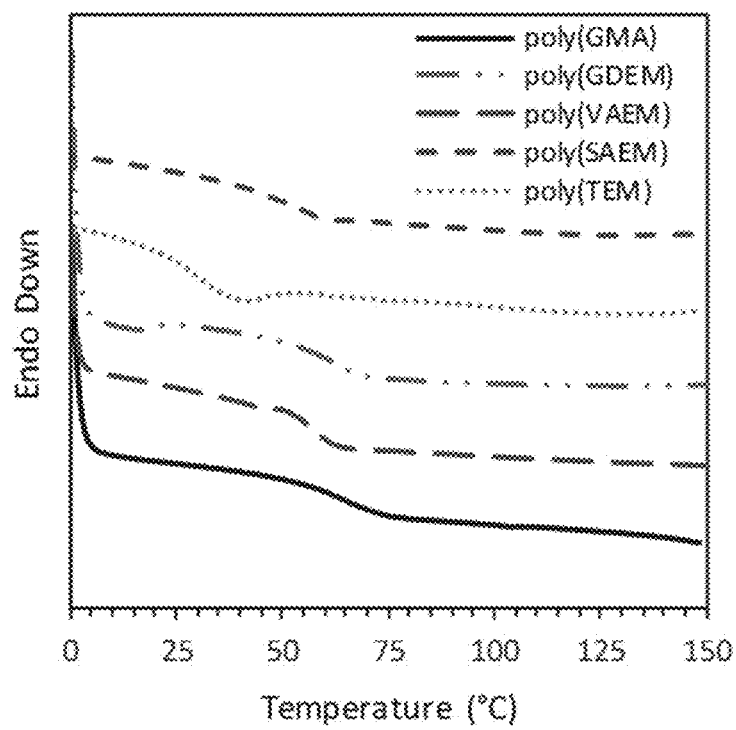
FIG. 9 is a graph illustrating DSC thermograms of the thermoplastic polymers. Vertically offset for clarity.
Figure 10:
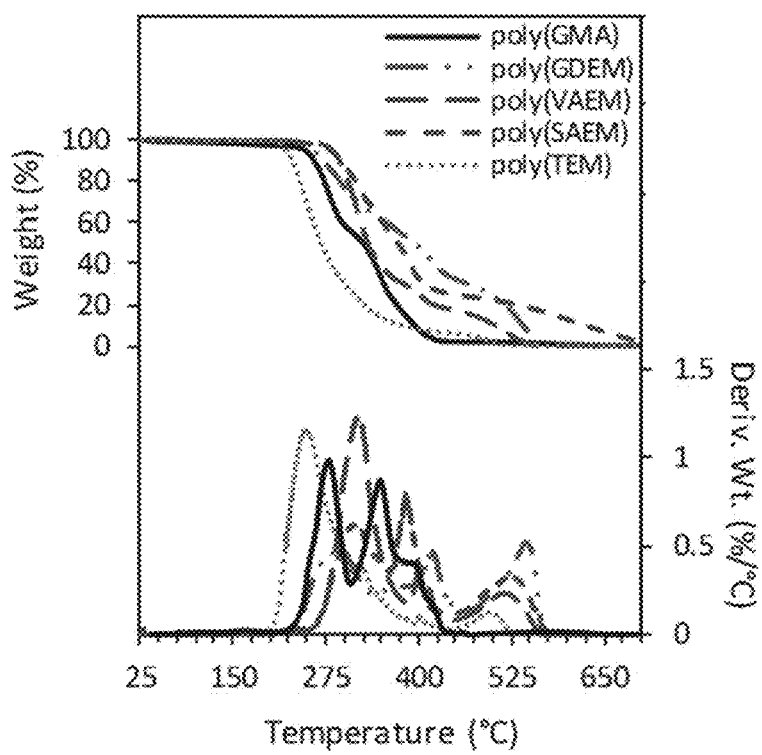
FIG. 10 is a graph illustrating TGA thermograms and the first derivatives of the thermoplastic polymers in oxidative environment (air).

The thermogravimetric properties of each homopolymer were analyzed using TGA in both $N_2$ and oxidative (air) atmospheres. The thermograms and first derivates of each polymer tested in $N_2$ are shown in FIG. 4. The thermograms and first derivatives of each polymer tested in air are available in FIGS. 4 and 10. The initial decomposition temperature (IDT), temperature at 50% degradation ($T_{50}$%), temperature at maximum degradation rate ($T_{max}$), and char content are listed in Table 2 for both $N_2$ and air atmospheres.

Most of the prepared homopolymers had considerably higher thermal stabilities than poly(GMA). Poly(GDEM), poly(VAEM), and poly(SAEM) had significantly higher IDT values than poly(GMA), likely due to the added aromaticity in the pendant chain enhancing thermal stability. Between poly(GDEM), poly(VAEM), and poly(SAEM), the placement and number of methoxy moieties had minimal effects on thermal stability; however, the added carbon on the pendant chain of poly(TEM) allows for a higher degree of rotation of the side group, subsequently decreasing the thermal stability below that of poly(GMA). The additional free rotation of the alkyl pendant group para to the ester moiety on the aromatic ring had a more consequential effect on the thermal properties than the methoxy moieties. Similar thermal degradation trends are seen in the $T_{50}\%$ and the $T_{max}$ data. The char content was similar for all of the homopolymers in both atmospheres. The thermogravimetric properties showed similar trends in both $N_2$ and air.

Homopolymerization of 4-(oxiran-2-ylmethoxy)benzyl methacrylate (GDEM)

GDEM (0.25 g), DMF (0.83 mL) and AIBN (0.0025 g) were added to a two-neck round bottom equipped with a magnetic stir bar. The mixture was sparged with argon for 15 minutes and heated to 60° C. for a minimum of 24 hours. The reaction mixture was precipitated into methanol, re-dissolved into DCM, and precipitated into hexanes to yield Poly(GDEM) as a white powder.

Homopolymerization of 3-methoxy-4-(oxiran-2-ylmethoxy)benzyl methacrylate (VAEM)

VAEM (0.25 g), DMF (0.83 mL) and AIBN (0.0025 g) were added to a two-neck round bottom equipped with a magnetic stir bar. The mixture was sparged with argon for 15 minutes and heated to 60° C. for a minimum of 24 hours. The reaction mixture was precipitated into methanol, re-dissolved into DCM, and precipitated into hexanes to yield Poly(VAEM) as a white powder.

A representative reaction scheme for the synthesis of homopolymers can be seen in Scheme 3:

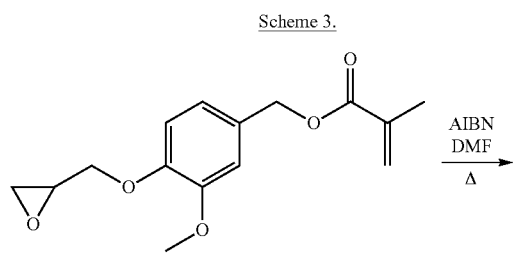

Scheme 3.

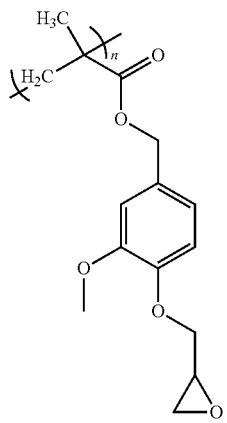

Homopolymerization of 3,5-dimethoxy-4-(oxiran-2-ylmethoxy)benzyl methacrylate (SAEM)

SAEM (0.28 g), DMF (0.95 mL) and AIBN (0.0028 g) were added to a two-neck round bottom equipped with a magnetic stir bar. The mixture was sparged with argon for 15 minutes and heated to 60° C. for a minimum of 24 hours. The reaction mixture was precipitated into methanol, re-dissolved into DCM, and precipitated into hexanes to yield Poly(SAEM) as a white powder.

Homopolymerization of 4-(oxiran-2-ylmethoxy)phenethyl methacrylate (TEM)

TEM (0.26 g), DMF (0.88 mL) and AIBN (0.0026 g) were added to a two-neck round bottom equipped with a magnetic stir bar. The mixture was sparged with argon for 15 minutes and heated to 60° C. for a minimum of 24 hours. The reaction mixture was precipitated into methanol, re-dissolved into DCM, and precipitated into hexanes to yield Poly(TEM) as a white powder.

TABLE 1

| Sample | $M_n$ (Da) | $M_w$ (Da) | Đ | $T_g$ (° C.) |
|---|---|---|---|---|
| poly(GMA) | 14,300 | 20,400 | 1.43 | 66 ± 1 |
| poly(GDEM) | 46,700 | 152,300 | 3.263 | 62 ± 1 |
| poly(VAEM) | 52,700 | 88,500 | 1.681 | 60 ± 5 |
| poly(SAEM) | 53,000 | 121,800 | 2.298 | 68 ± 1 |
| poly(TEM) | 46,900 | 151,900 | 3.239 | 46 ± 1 |

TABLE 2

| Sample | N₂ | | | | Air | | | |
|---|---|---|---|---|---|---|---|---|
| | IDT (°C.) | $T_{50\%}$ (°C.) | $T_{max}$ (°C.) | Char Content (%) | IDT (°C.) | $T_{50\%}$ (°C.) | $T_{max}$ (°C.) | Char Content (%) |
| poly(GMA) | 236 ± 11 | 327 ± 2 | 278 ± 2 | 0.7 ± 0.4 | 248 ± 1 | 309 ± 1 | 287 ± 1 | 0.4 ± 0.2 |
| poly(GDEM) | 261 ± 1 | 365 ± 6 | 307 ± 1 | 0.1 ± 0.1 | 260 ± 1 | 398 ± 5 | 294 ± 1 | 0.3 ± 0.3 |
| poly(VAEM) | 288 ± 1 | 335 ± 1 | 330 ± 1 | 0.2 ± 0.1 | 287 ± 3 | 335 ± 5 | 320 ± 2 | 0.4 ± 0.1 |
| poly(SAEM) | 281 ± 2 | 368 ± 6 | 388 ± 8 | 0.3 ± 0.2 | 282 ± 1 | 379 ± 4 | 383 ± 1 | 0.1 ± 0.1 |
| poly(TEM) | 217 ± 5 | 294 ± 7 | 325 ± 1 | 0.5 ± 0.1 | 223 ± 1 | 268 ± 1 | 248 ± 1 | 0.3 ± 0.1 |

Initial decomposition temperature (IDT),
temperature at 50% weight loss ($T_{50\%}$),
temperature at maximum decomposition rate ($T_{max}$)

Example 1

Synthesis and Characterization of Novel Glycidyl Methacrylate Monomers

The starting molecule, epichlorohydrin, and TEBAC were added to a three-neck round bottom equipped with a mechanical mixer. The reaction mixture was heated to 80° C. for 1 hour. After the 1 hour, the reaction was cooled to room temperature and a mixture of 5 M NaOH and TEBAC was added dropwise. The reaction was then worked up and washed with a solution of equal parts DI water and ethyl acetate. Flash chromatography was used to purify the mono-glycidyl ether product. The mono-glycidyl ether product was added to a three-neck round bottom with DCM and triethylamine in an ice bath with a dropping funnel and an inlet for dry argon gas. Once the contents were cooled to 0° C., a DCM and methacryloyl chloride solution was added dropwise with constant stirring. After 24 hours, DCM was added to the mixture and then washed once with 2.5 M NaOH solution. The organic phase was isolated, and solvent removed using reduced pressure. The dual functional product was further purified using flash chromatography.

Example 2

Synthesis and Characterization of Novel Homopolymers

The dual functional monomer of choice was dissolved in DMF (3.32 mL per g of monomer) and AIBN (1 wt % of dual functional monomer) was added to a two-neck round bottom equipped with a magnetic stir bar. The mixture was sparged with argon for 15 minutes and heated to 60° C. for a minimum of 24 hours. The reaction mixture was precipitated into methanol, re-dissolved into DCM, and precipitated into hexanes to yield the homopolymerized dual functional monomers as white powders.

Example 3

Synthesis and Characterization of Interpenetrating Polymer Networks

IPNs were prepared by formulating a dual functional monomer with other monomers and crosslinkers of epoxy and methacrylate moieties including DGEBA, EGDMA, Styrene, and 4, 4' diaminodicyclohexyl methane (Amicure PACM) in varying weight ratios.

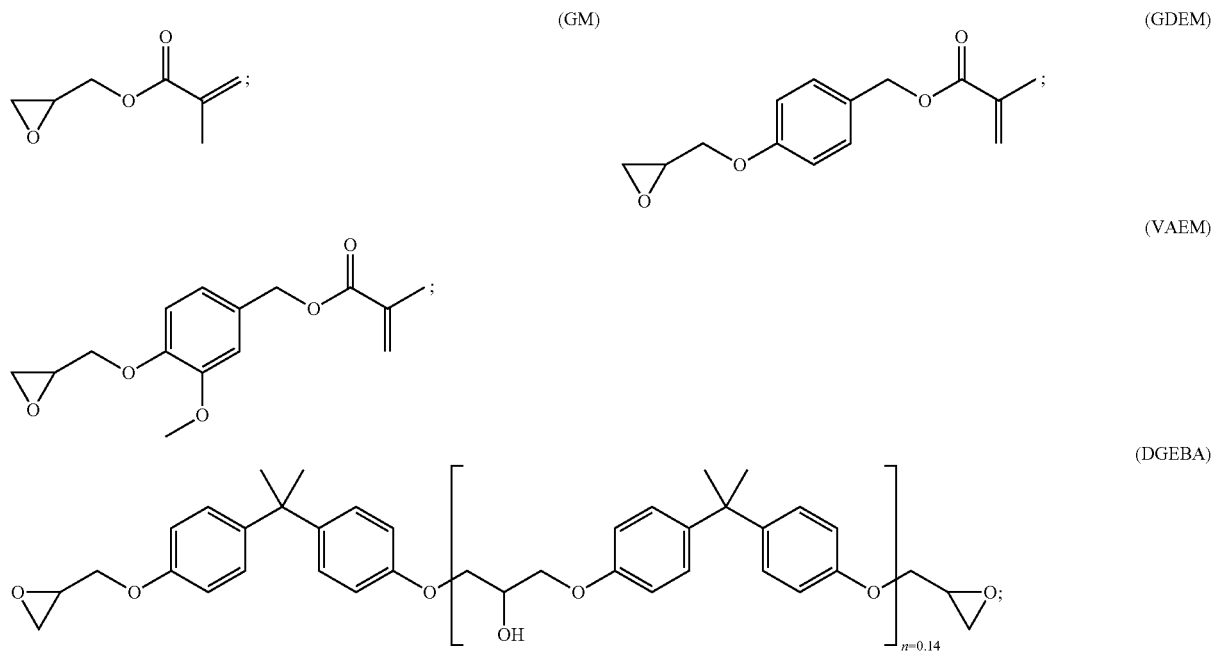

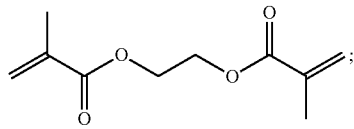 (EGDMA)

TABLE 3

| System | Methacrylate % Conversion | Epoxy % Conversion |
| --- | --- | --- |
| 50:0:50 DGEBA:GM:EGDMA | 79.4 | 95.2 |
| 50:25:50 DGEBA:GM:EGDMA | 79.3 | 98.9 |
| 50:25:50 DGEBA:GDEM:EGDMA | 98.6 | 99.1 |
| 50:25:50 DGEBA:VAEM:EGDMA | 86.4 | 97.7 |

TABLE 4

| System | E' @ 25° C. Gpa | Peak of E" (T) (° C.) | Peak of tan δ (° C.) | ρ @ 25° C. (g cm$^{-3}$) |
| --- | --- | --- | --- | --- |
| 50:0:50 DGEBA:GM:EGDMA | 2.83 | 101.0 | 111.4 | 1.165 |
| 50:25:50 DGEBA:GM:EGDMA | 2.54 | 106.1 | 128.2 | 1.167 |
| 50:25:50 DGEBA:GDEM:EGDMA | 2.92 | 111.9 | 131.7 | 1.163 |
| 50:25:50 DGEBA:VAEM:EGDMA | 3.10 | 131.1 | 147.0 | 1.178 |

The disclosures of each and every patent, patent application, and publication cited herein are hereby incorporated herein by reference in their entirety. While this invention has been disclosed with reference to specific embodiments, it is apparent that other embodiments and variations of this invention can be devised by others skilled in the art without departing from the true spirit and scope of the invention. The appended claims are intended to be construed to include all such embodiments and equivalent variations.

What is claimed is:

1. A monomer selected from the group consisting of:

a compound of formula:

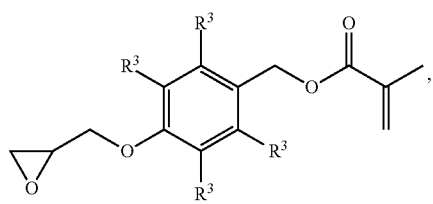

wherein each instance of $R^3$ is independently selected from the group consisting of H, optionally substituted $C_1$-$C_6$ alkyl, and optionally substituted $C_1$-$C_6$ alkoxy;

a compound of formula:

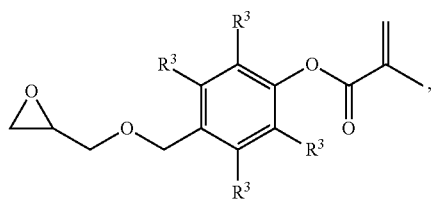

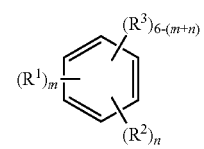

wherein each instance of $R^3$ is independently selected from the group consisting of H, optionally substituted $C_1$-$C_6$ alkyl, and optionally substituted $C_1$-$C_6$ alkoxy;

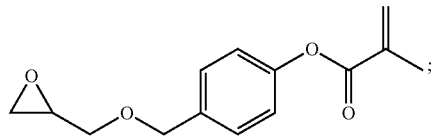

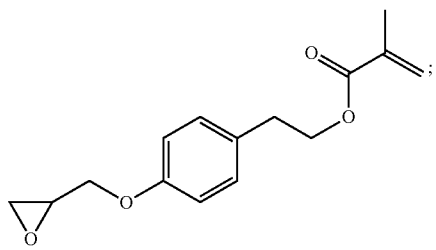

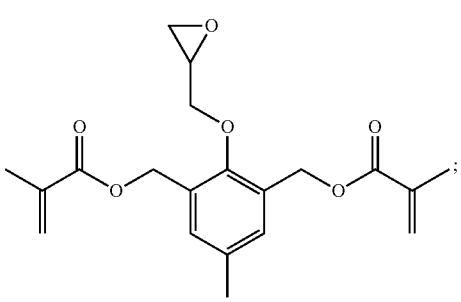

-continued

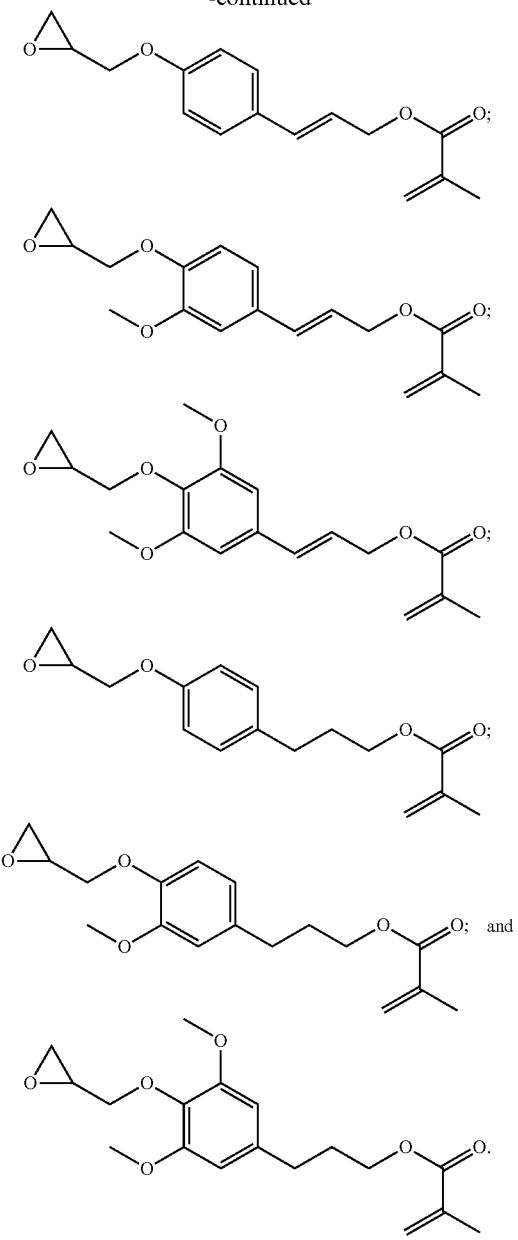

2. A composition comprising at least one monomer of claim 1.

3. The composition of claim 2, further comprising at least one polymerization initiator.

4. The composition of claim 3, wherein the at least one polymerization initiator is at least one selected from the group consisting of photoinitiators, thermal initiators, and redox initiators, with or without an accelerator.

5. The composition of claim 2, further comprising at least one additional compound comprising at least one selected from the group consisting of an epoxide functionality, a methacrylate functionality, a vinyl functionality, an acrylate functionality, an allylic functionality, a cyclic carbonate functionality, a thiol functionality, an amine functionality, an aniline functionality, an anhydride functionality, a carboxylic acid functionality, and an unsaturated polyester.

6. The composition of claim 5, wherein the at least one additional compound is selected from the group consisting of bisphenol A diglycidyl ether, bisphenol F diglycidyl ether, bisguaiacol diglycidyl ether, novolac epoxies, glycidyl ethers of hydrogenated bisphenols and epoxides, di(cyclohexane epoxidemethyl)ether, epoxy cyclohexyl methyl-epoxy cyclohexane carboxylate, 4,4'-diaminodicyclohexylmethane (PACM), diethylmethylbenzenediamine, Jeffamine, polyetheramines, amidoamines, aminopolyamide, diethyltriamine, triethylenetetramine, tetraethylenepentamine, diethylaminopropylamine, trimethylhexamethylenediamine, dipropyltriamine piperidine, N-aminopiperidine, menthanediamine, isophoronediamine, diaminodiphenylsulfone, methylene dianiline, oxydianiline, imidazole, dicyandiamide, ethylene glycol dimethacrylate (EGDMA), hexanediol dimethacrylate (HDDMA), methyl methacrylate (MMA), styrene, glycidyl methacrylate, vinyl esters of bisphenol A diglycidyl ether, bisphenol F diglycidyl ether, glycidyl ethers of hydrogenated bisphenols, novalac epoxies, isobornyl acrylate, isosorbide (meth)acrylate, methacrylated lauric acid, lauryl (meth)acrylate, cyclohexyl methacrylate, furfuryl methacrylate, phthalic anhydride, hexahydrophthalic anhydride, nadic anhydride, nadic methyl anhydride, dodecenylsuccinic anhydride, maleic anhydride, tetrahydrophthalic anhydride, pyromellitic anhydride, trimellitic anhydride, benzophenonetetracraboxylic dianahydride, chlorendic anhydride, hexamethylene diisocyanate, isophorone diisocyanate, methylenediphenyl diisocyanate, and bisphenol A cyclic carbonate.

7. A composition comprising at least one monomer of claim 1, further comprising:
at least one additional first monomer capable of forming with the at least one monomer a first polymer comprising linkages selected from the group consisting of epoxy linkages, epoxy-amine linkages, and any combinations thereof; and
at least one additional second monomer capable of forming with the at least one monomer a second polymer comprising linkages selected from the group consisting of acrylate linkages, methacrylate linkages, vinyl linkages, and any combinations thereof.

8. The composition of claim 2, wherein the monomer is selected from the group consisting of:

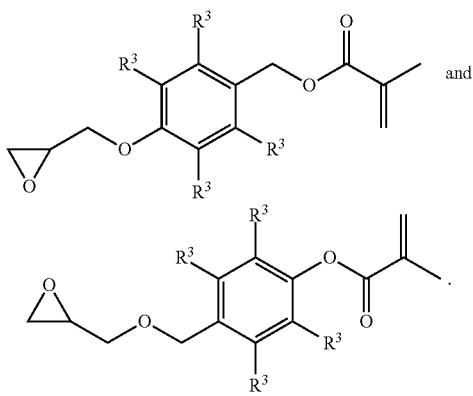

9. The composition of claim 2, wherein the monomer is selected from the group consisting of:

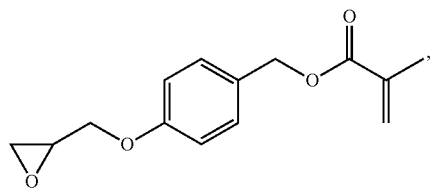

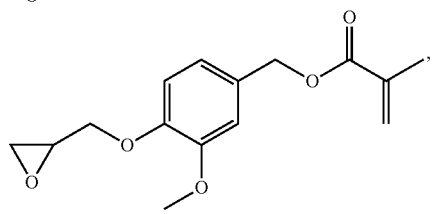

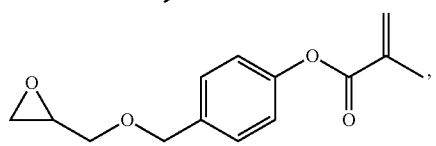

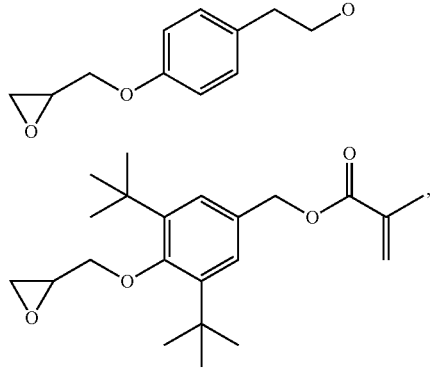

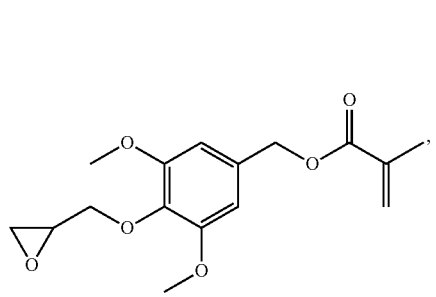

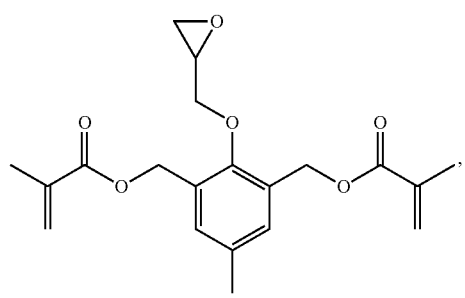

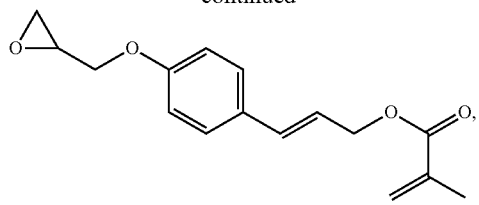

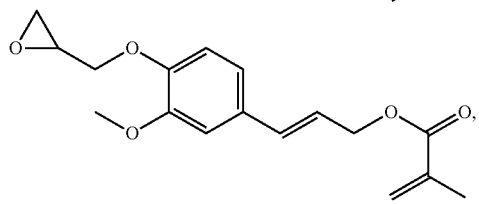

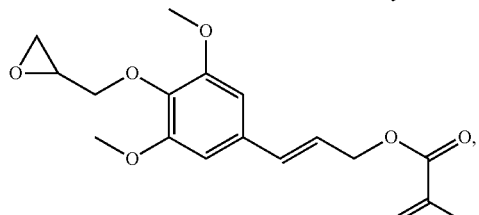

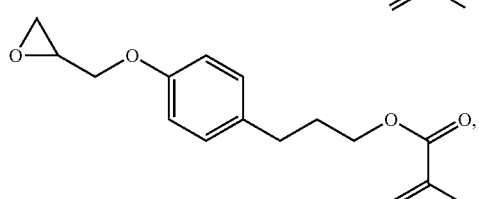

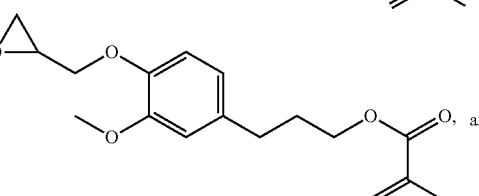

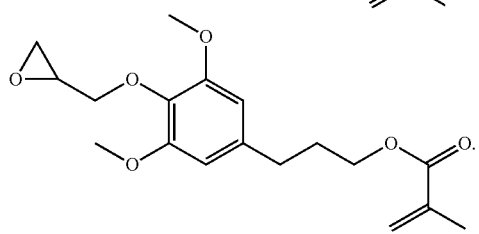, and

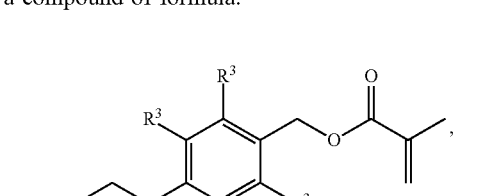

10. A kit comprising:
a first composition comprising at least one monomer selected from the group consisting of
a compound of formula:

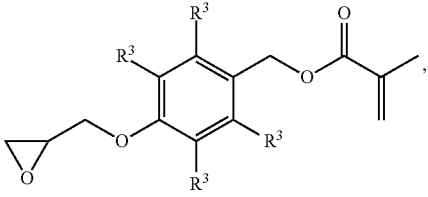

wherein each instance of $R^3$ is independently selected from the group consisting of H, optionally substituted $C_1$-$C_6$ alkyl, and optionally substituted $C_1$-$C_6$ alkoxy;

a compound of formula:

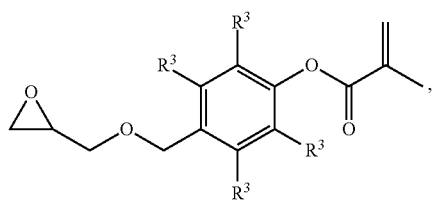

wherein each instance of $R^3$ is independently selected from the group consisting of H, optionally substituted $C_1$-$C_6$ alkyl, and optionally substituted $C_1$-$C_6$ alkoxy;

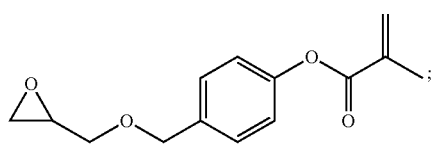

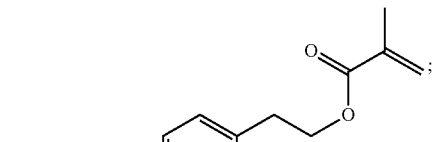

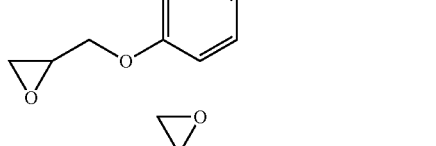

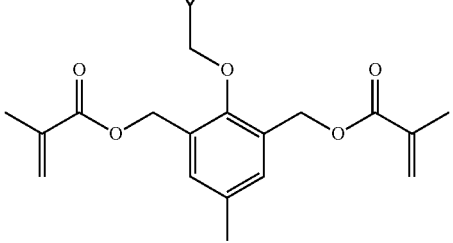

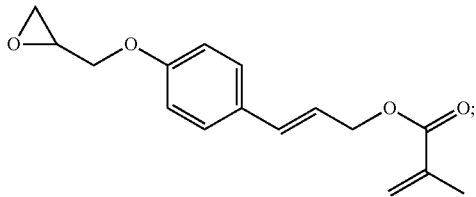

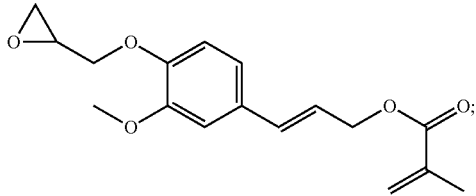

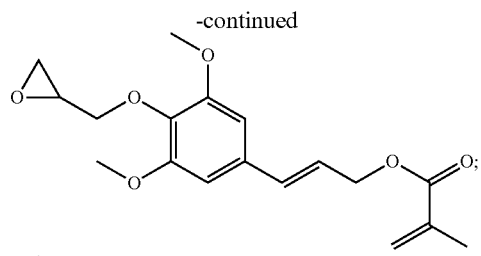

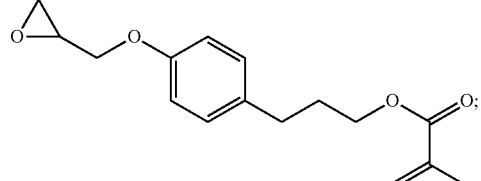

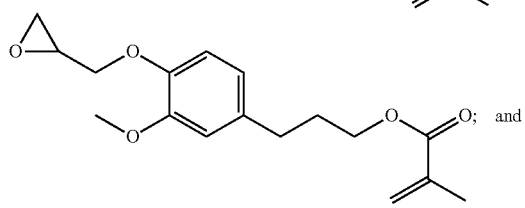

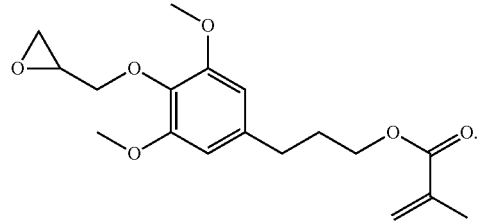

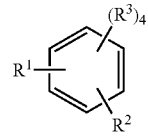

a second composition comprising at least one first additional monomer capable of forming with the at least one monomer in the first composition a first polymer comprising linkages selected from the group consisting of epoxy linkages, epoxy-amine linkages and any combinations thereof;

a third composition comprising at least one second additional monomer capable of forming with the at least one monomer in the first composition a second polymer comprising linkages selected from the group consisting of methacrylate linkages, vinyl linkages, any combination thereof; and instructional material for forming an interpenetrating polymer network using the compositions of the kit.

* * * * *